United States Patent [19]
Capaccio et al.

[11] Patent Number: 5,746,733
[45] Date of Patent: May 5, 1998

[54] SYRINGE FILLING AND DELIVERY DEVICE

[75] Inventors: Paul R. Capaccio, Clifton; Gary Cohen, Highland Lakes; Alvin T. Olsen, Caldwell; Mark C. Yale, Westwood, all of N.J.

[73] Assignee: Becton, Dickinson and Company, Franklin Lakes, N.J.

[21] Appl. No.: 839,224

[22] Filed: Apr. 22, 1997

Related U.S. Application Data

[63] Continuation-in-part of Ser. No. 681,253, Jul. 22, 1996, which is a continuation-in-part of Ser. No. 245,934, May 19, 1994, abandoned.

[51] Int. Cl.$^6$ .................................................. A61M 5/00
[52] U.S. Cl. .................. 604/411; 604/240; 141/329
[58] Field of Search ................. 604/411, 240–243, 604/200, 201, 202, 89, 88, 905; 141/329, 330, 363

[56] References Cited

U.S. PATENT DOCUMENTS

| | | | |
|---|---|---|---|
| 4,613,329 | 9/1986 | Bodicky | 604/243 |
| 4,781,701 | 11/1988 | Geprags | 604/240 |
| 5,002,538 | 3/1991 | Johnson | 604/240 |
| 5,135,513 | 8/1992 | Meyer et al. | 604/411 X |
| 5,336,192 | 8/1994 | Palestrant | 604/200 |
| 5,385,546 | 1/1995 | Kriesel et al. | 604/411 |
| 5,389,086 | 2/1995 | Attermeier et al. | 604/240 X |

*Primary Examiner*—John D. Yasko
*Attorney, Agent, or Firm*—John L. Voellmicke

[57] ABSTRACT

A fluid transfer device for accessing fluid from vials and ampoules includes a cannula assembly including a cannula having a lumen therethrough connected to a hub having an open proximal end. A filling straw includes a proximal end, a distal end, and a passageway therethrough. The straw further includes a needle portion at the distal end and a shaft portion between the needle portion and the proximal end. A cutting edge is provided at the distal end of the needle portion for piercing a vial stopper. The cannula assembly is removably engaged with the filling straw so that the open proximal end of the hub is in fluid communication with the passageway of the filling straw. An elongate shield having an open proximal end, an open distal end and a side wall therebetween defining a recess in the shield. The shield is removably connected to the straw so that the shaft portion and the needle portion of the straw are contained within the recess. A seal plug having a proximal end and a distal end is provided. The seal plug has a distal position with respect to the shield wherein the seal plug projects distally outwardly from the distal end of the shield for telescoping movement from the distal position to a proximal position wherein the seal plug seals the needle portion to prevent unpressurized fluid communication between the passageway and the exterior of the shield.

17 Claims, 26 Drawing Sheets

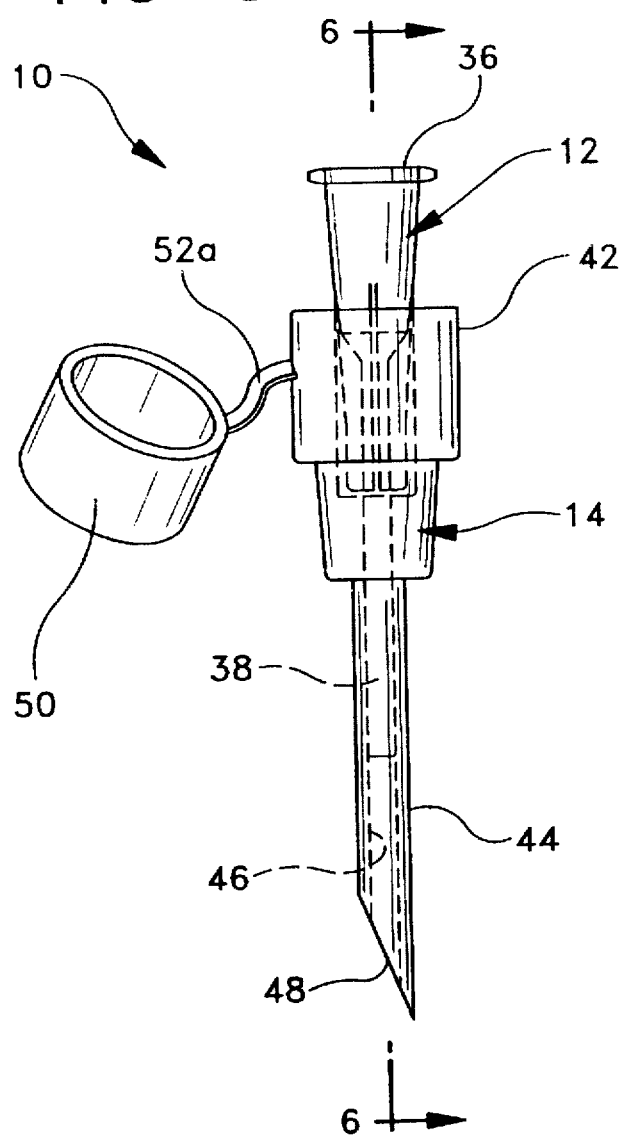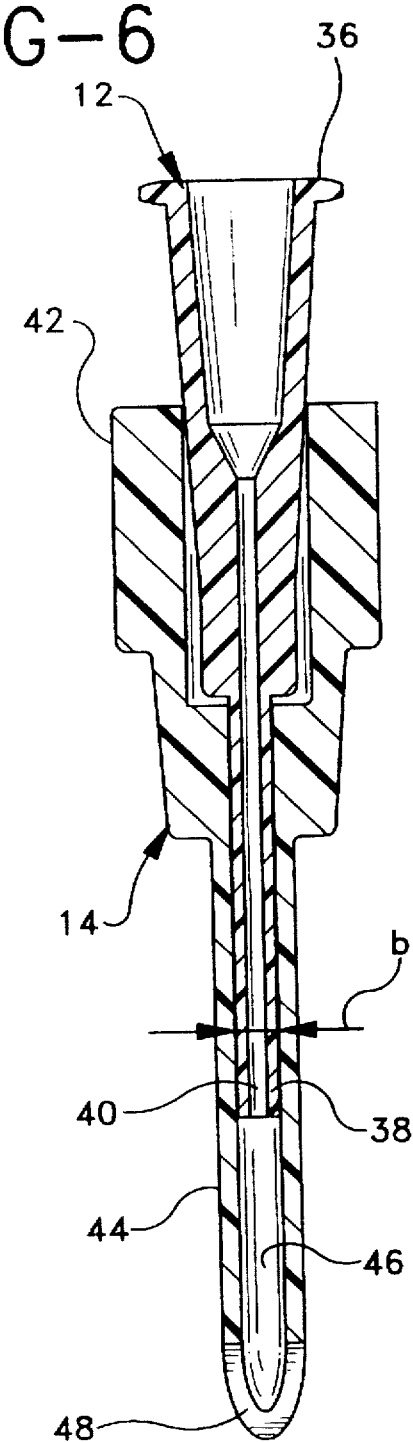

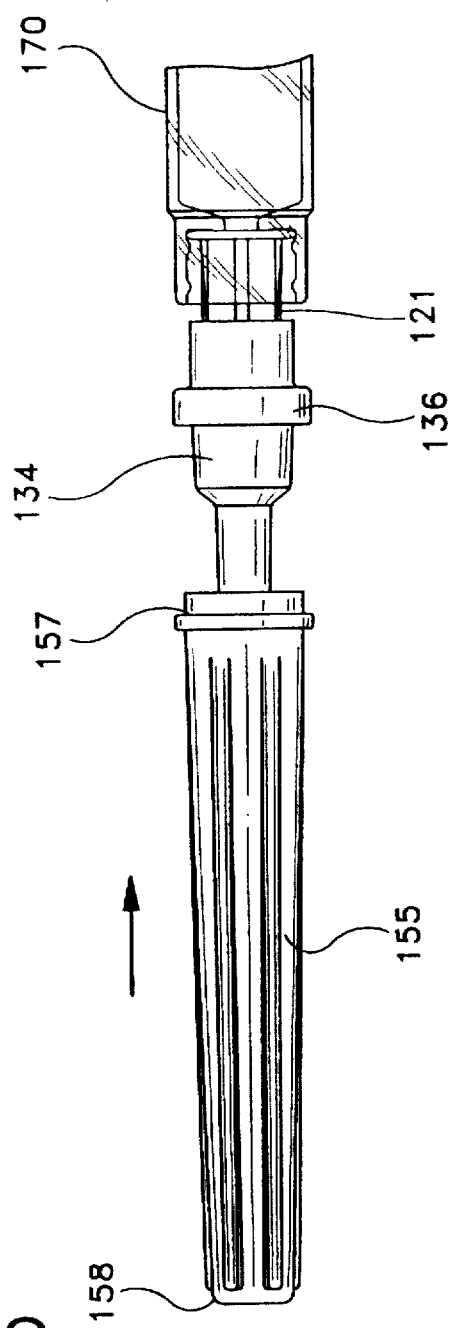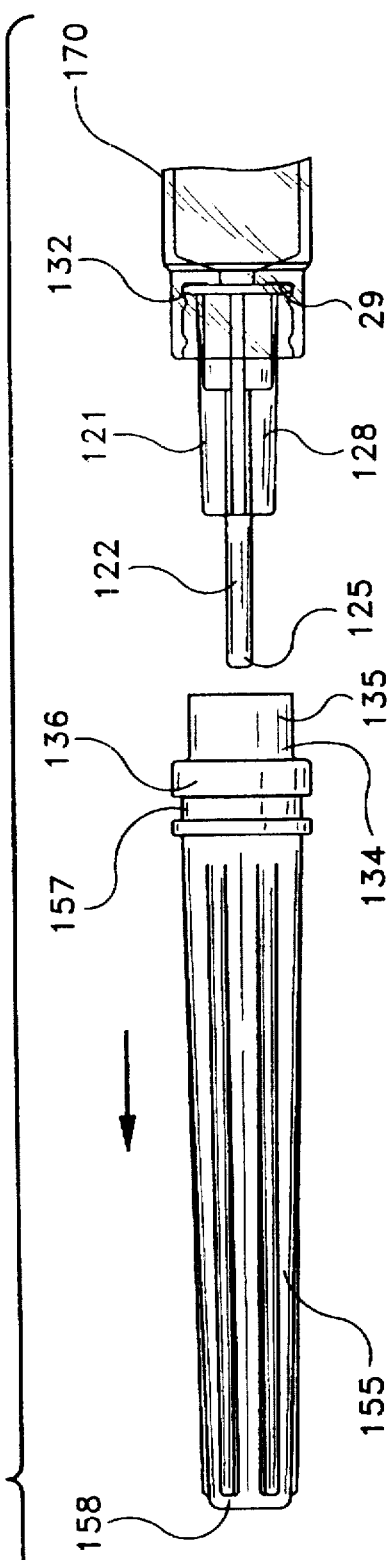
FIG-16
FIG-17

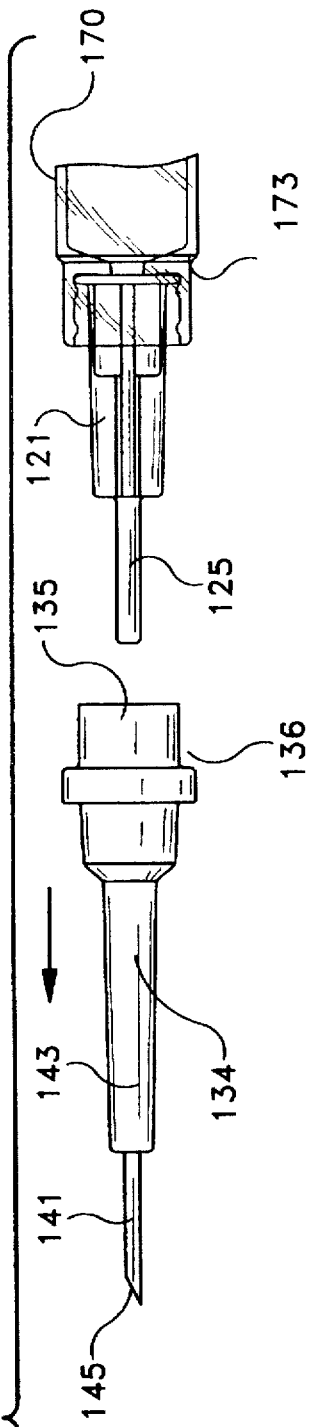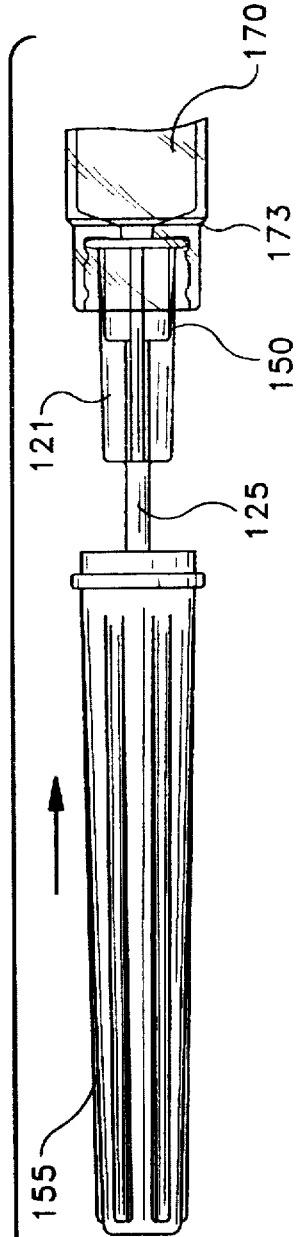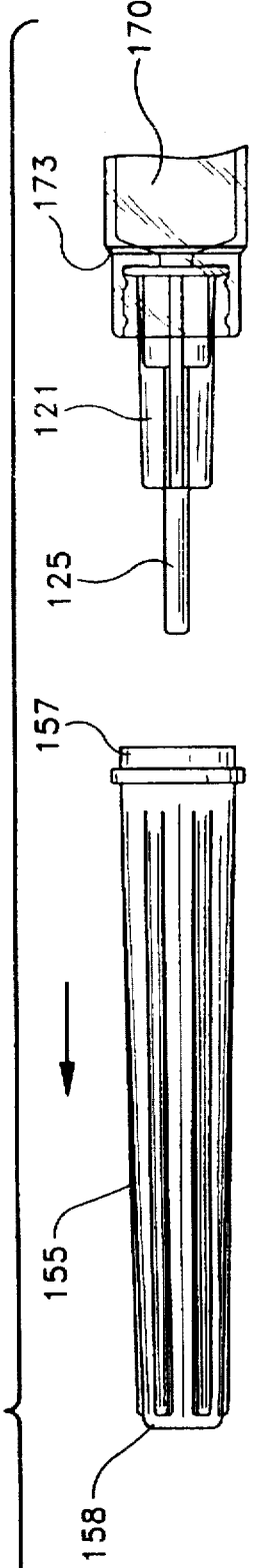

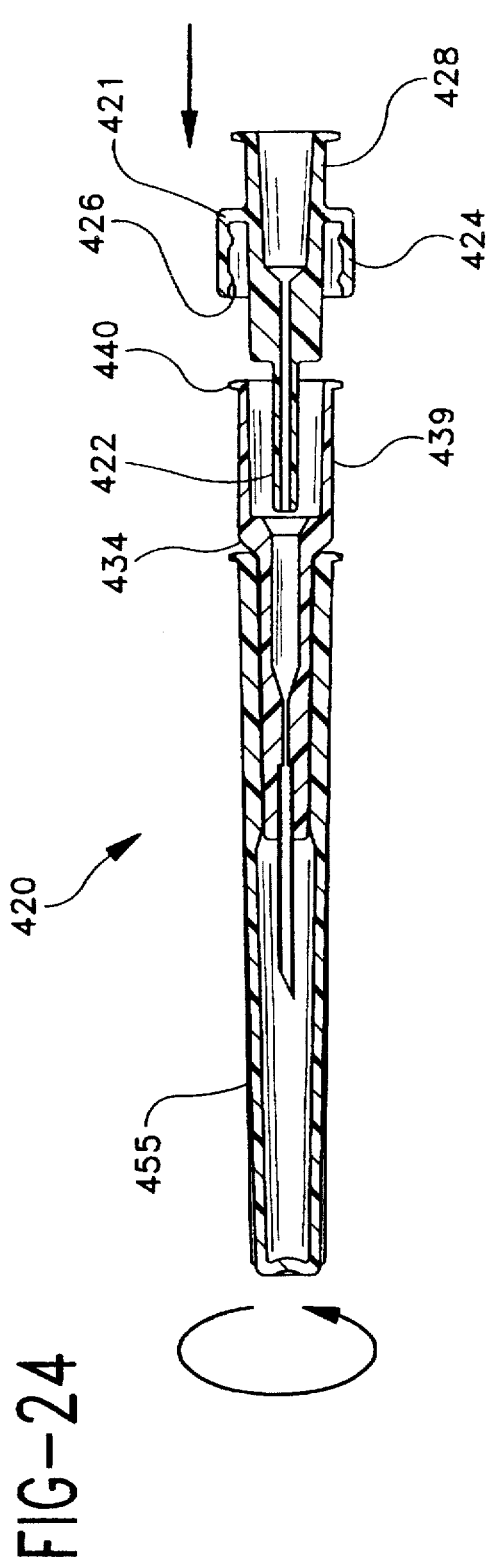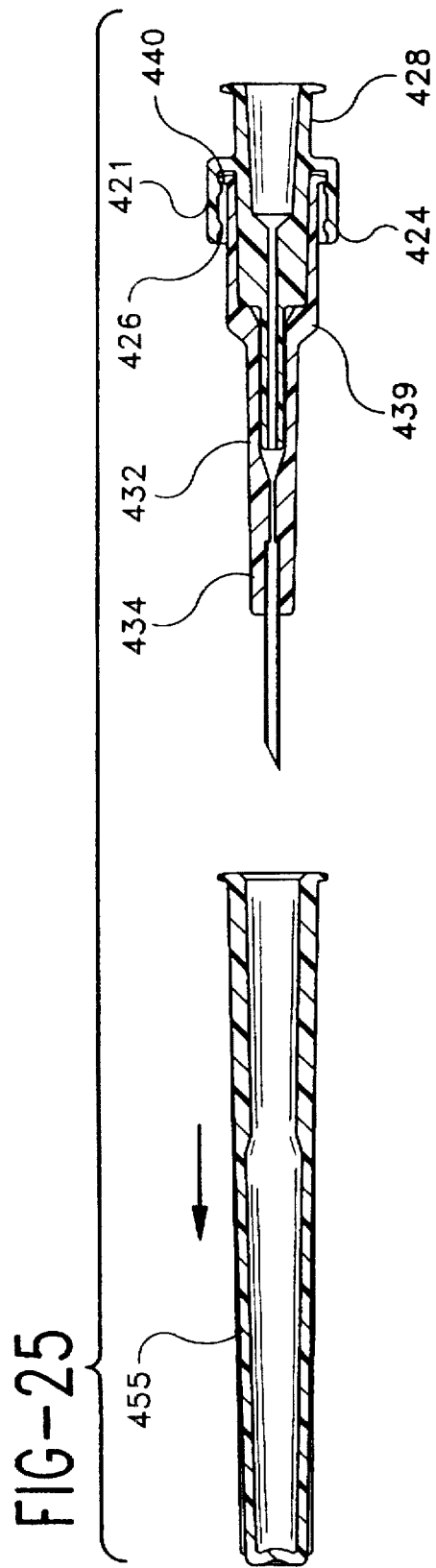
FIG-24
FIG-25

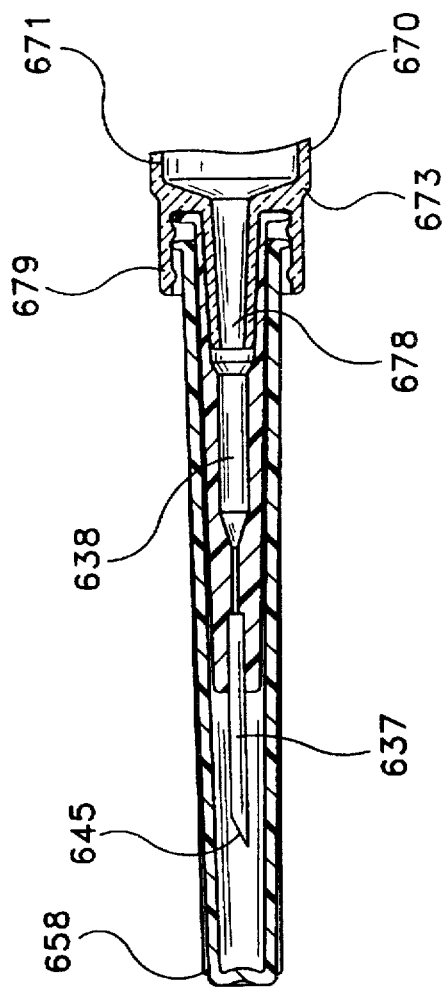
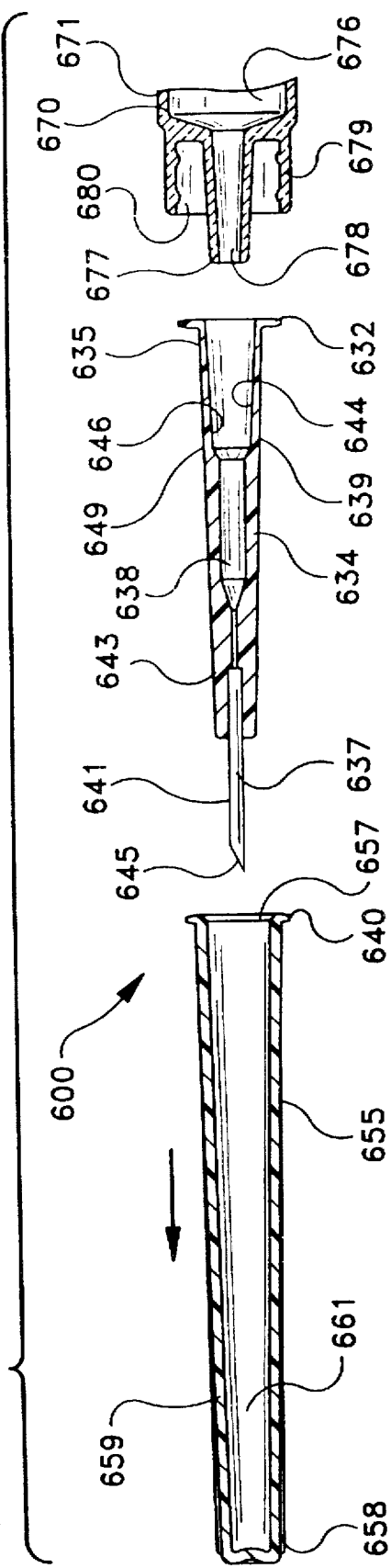
FIG-27
FIG-28

SYRINGE FILLING AND DELIVERY DEVICE

CROSS-REFERENCE TO RELATED APPLICATIONS

This patent application is a continuation-in-part of U.S. patent application Ser. No. 681,253 filed on Jul. 22, 1996, which is a continuation-in-part of U.S. patent application Ser. No. 245,934 filed on May 19, 1994 now abandoned.

FIELD OF THE INVENTION

The subject invention relates to a device mountable on a hypodermic syringe or other fluid delivery device which enables access to medication or injectable liquid in either glass ampoules or in vials having elastomeric closures and the subsequent delivery of medication or injectable liquid.

BACKGROUND

A typical hypodermic syringe includes a syringe barrel with a mounting collar for threadedly engaging the hub of a needle cannula. The hub and the needle cannula are connected to one another or are maintained separately from the syringe barrel until shortly prior to use. In cases where the needle is maintained separately, the medical practitioner selects an appropriate needle assembly for the procedure being carried out. The needle assembly is removed from its sterile package, and the hub of the needle assembly is threadedly engaged with the mounting collar of the syringe barrel.

Liquid pharmaceuticals and other injectable liquids are often stored in rigid containers which can be accessed using a hypodermic syringe. Some containers for liquid pharmaceuticals are plastic or glass vials with an elastomeric closure that can be penetrated by the needle of a hypodermic syringe. To access the liquid in a vial, the medical practitioner moves the plunger of the hypodermic syringe in a proximal direction to draw into the syringe barrel a volume of air substantially equal to the volume of medication that is desired. The open distal end of the needle is then urged through the elastomeric closure of the vial, and the air in the syringe barrel is injected into the vial. The distal tip of the needle and the vial engaged therewith are then pointed gravitationally upwardly. The practitioner ensures that the distal tip of the needle is covered by the medication in the vial by manipulating the needle and the vial with respect to each other. The plunger of the hypodermic syringe is then moved proximally to draw the medication through the needle and into the chamber of the syringe barrel.

After withdrawing a desired dose of medication from a vial, the medical practitioner may inject the medication into either a patient, another vial or into an injection site of an intravenous set or catheter. There is a trend toward needleless I.V. systems which do not require a pointed needle cannula to piece the injection site of an I.V. set. There are many systems that have injection sites covered by a pre-slit septum which can be accessed by a blunt cannula. Accordingly, after withdrawing medication from a vial using a sharp needle the user must remove the needle and install a blunt cannula if the medication will be used with an I.V. set. The user runs the risk of accidental needle stick using the needle to draw the medication into the syringe and in the act of removing the needle to replace it with a blunt cannula. Also, there is the potential of contaminating the components when they are installed and removed during the filling and delivery process. Accordingly, there is a need for a device which will allow filling of a syringe from a vial having a pierceable stopper without the use of a very sharp needle and the subsequent delivery of the medication to an I.V. set through a blunt cannula without having to handle or reshield sharp needles.

Plastic vials and elastomeric closures for vials are somewhat gas permeable. Some pharmaceutical products will degrade rapidly in the presence of even small amounts of gas. Hence, these pharmaceuticals typically are stored in glass ampoules. The frangible end of a glass ampoule can be snapped off to enable access to the medication stored therein. The medical practitioner may withdraw the medication by inserting the tip of the needle on a hypodermic syringe into the medication stored in the ampoule. The plunger of the hypodermic syringe is then moved proximally to draw the liquid medication in the ampoule through the needle and into the barrel of the hypodermic syringe. The hypodermic syringe may then be withdrawn from the ampoule and used in substantially the manner described above. The ampoule typically is held with the open top gravitationally upwardly while the hypodermic syringe is being filled. This needle length required for ampoule filling may substantially exceed the length of the needle conveniently required for subsequent use for injections. Likewise, the same or similar problems exist where the medication obtained from an ampoule will be subsequently injected into an injection site having a pre-slit septum since the needle must be installed and removed from the syringe and the new blunt cannula installed. Thus, there are risks with accidental contamination and needle sticks before the properly filled syringe and blunt cannula combination are prepared.

SUMMARY OF THE INVENTION

The subject invention relates to a device for safety and efficiently filling a hypodermic syringe. The device may include a blunt cannula having opposed proximal and distal ends. The proximal end is configured for engagement with the distal end of the hypodermic syringe. For example, the proximal end of the blunt cannula may include projections for threadedly engaging a luer collar at the distal end of the syringe barrel. The distal end of the cannula may be blunt and may be configured for selective mating with a prior art fitting of an intravenous line.

The device further comprises a vial access spike which has opposed proximal and distal ends and a communication passage extending axially therethrough. The proximal end of the vial access spike is releasably mounted in fluid-tight engagement with the distal end of the blunt cannula. For example, the proximal end of the passage through the vial access spike may be frictionally secured in fluid-tight engagement over the distal end of a blunt cannula. The distal end of the vial access spike defines a beveled tip that is sharp enough to pierce the rubber stopper of a vial, but preferably not sharp enough to pierce skin through incidental contact. The vial access spike may further include a cap for selective sealing engagement over the proximal end of the spike. The cap may be unitarily connected to the vial access spike by a hinge or a tether. A hinged connection may be defined by an over-center hinge which is stable in a fully open or fully closed position of the cap. However the over-center hinge will be biased at intermediate positions to urge the cap into either the fully opened or fully closed position.

The device may further comprise a protective shield that can be mounted over at least the distal end of the vial access spike. The protective shield may have a slot to surround the hinge or tether. The shield prevents contamination of the beveled distal tip of the spike prior to insertion into the vial.

The assembled blunt cannula, vial access spike and shield may be packaged separately from the hypodermic syringe. Alternatively, the assembled blunt cannula and vial access spike may be mounted on and packaged with the hypodermic syringe.

A hypodermic syringe that has the subject filling device mounted thereto may be filled by removing the shield from the vial access spike and driving the beveled distal end of the vial access spike through the vial stopper. The hypodermic syringe and the vial may then be inverted, such that the liquid medication in the vial covers the distal end of the vial access spike. The plunger of the hypodermic syringe may then be pulled in a proximal direction to draw fluid into the syringe barrel. The user may then separate the connected hypodermic syringe and blunt cannula from the vial access spike, and the connected hypodermic syringe and blunt cannula may be used in the conventional manner. The vial access spike will remain in the vial, and the cap can be engaged over the proximal end of the spike to seal the vial for subsequent access.

A fluid transfer device for accessing fluid from vials and ampoules of the present invention comprises a cannula assembly including a cannula having a proximal end, a distal end and a lumen therethrough, and a hub having an open proximal end and a distal end joined to the proximal end of the cannula so that the lumen is in fluid communication with the open proximal end of the hub. A filling straw having a proximal end, a distal end, and a passageway therethrough includes a housing at the proximal end, a needle portion at the distal end and a shaft portion therebetween. A ledge between the needle portion and the shaft portion is provided for limiting the depth of penetration of the needle portion into a vial stopper. The housing includes a cavity in its proximal end in fluid communication with the passageway. A cutting edge at the distal end of the needle portion is provided for piercing a vial stopper. Structure is provided for removably engaging the cannula assembly with the housing so that the open end of the hub is in fluid communication with the passageway of the filling straw and the cannula is within the cavity. A shield having an open proximal end, a distal end, and a side wall therebetween defining a recess in the shield is removably connected to the straw so that the shaft portion and the needle portion of the straw are contained within the recess.

A fluid transfer device of the present invention comprises a cannula assembly including a cannula having a proximal end, a distal end and a lumen therethrough. A hub having an open proximal end and a distal end is joined to the proximal end of the cannula so that the lumen is in fluid communication with the open proximal end of the hub. A filling straw includes a proximal end, a distal end and a passageway therethrough. The straw includes a needle portion at its distal end and a shaft portion between the needle portion and the proximal end. A cutting edge at the distal end of the needle portion is provided for piercing a vial stopper. The cannula assembly and the filling straw are removably engaged so that the proximal end of the hub is in fluid communication with the passageway of the filling straw. A shield has an open proximal end, an open distal end and a side wall therebetween defining a recess in the shield. The shield is removably connected to the filling straw so that the needle portion and substantially all of the shaft portion are contained within the recess; and a seal plug has a proximal end and a distal end. The seal plug has a distal position where the seal plug projects distally outwardly from the distal end of the shield for telescoping movement from the distal position to a proximal position wherein the seal plug seals the needle portion to prevent unpressurized fluid communication between the passageway and the exterior of the shield.

Another embodiment of the present invention includes a method for transferring injectable liquid including the steps of:

(a) providing a syringe including a syringe barrel having an elongate cylindrical body defining a chamber for retaining fluid, an open proximal end, a distal end and a tip extending from the distal end having a tip passageway therethrough in fluid communication with the chamber, a stopper in fluid-tight slidable engagement inside the barrel and an elongate plunger rod connected to the stopper and extending proximally through the open end of the barrel;

(b) providing a syringe filling device comprising a cannula assembly including a cannula having a proximal end, a blunt distal end and a lumen therethrough, and a hub having an open proximal end and a distal end joined to the proximal end of the cannula so that the lumen is in fluid communication with the open proximal end of the hub; a filling straw having a proximal end, a distal end and a passageway therethrough, the straw including a housing at the proximal end, a needle portion at the distal end and a shaft portion therebetween, the housing having a cavity in its proximal end in fluid communication with the passageway, a cutting edge on the distal end of the needle portion for piercing a vial stopper, the cannula assembly being removably engaged with the housing so that the open proximal end of the hub is in fluid communication with the passageway of the filling straw and the cannula is within the cavity; a shield having an open proximal end, an open distal end and a side wall therebetween defining a recess in the shield, the shield being removably connected to the straw so that the shaft portion and the needle portion are contained within the recess; and a seal plug having a proximal end and a distal end, the seal plug having a distal position wherein the seal plug projects distally outwardly from the distal end of the shield for telescoping movement from the distal position to a proximal position wherein the seal plug seals the needle portion to prevent unpressurized fluid communication between the passageway and the exterior of the shield (c) connecting the syringe filling device to the syringe so that the tip is positioned within the open proximal end of the hub and the chamber is in fluid communication with the cannula;

(d) providing a vial having a pierceable septum and containing an injectable liquid;

(e) removing the shield from the straw;

(f) piercing the pierceable septum of the vial with the needle portion of the filling straw to establish fluid communication between the interior of the vial and the chamber of the syringe;

(g) withdrawing the desired amount of injectable liquid from the vial into the chamber by moving the plunger rod in a proximal direction with respect to the barrel; and (h) withdrawing the needle portion from the septum of the vial; and (i) reconnecting the shield to the straw so that the needle portion and substantially all of the shaft portion of the straw are contained within the recess of the shield; and (j) moving the seal plug from the distal position to the proximal position to seal the needle portion.

BRIEF DESCRIPTION OF THE DRAWINGS

FIG. 5 is a side elevational view similar to FIG. 2, but showing an alternate vial access spike.

FIG. 6 is a cross-sectional view of the blunt cannula and vial access spike of FIG. 5 taken along line 6—6.

FIGS. 16 and 17 illustrate steps in a method of use of the present invention between filling and dispensing of injectable liquid.

FIGS. 18–20 illustrate steps in another method of use of the present invention between filling and dispensing of injectable liquid.

FIGS. 24 and 25 are side elevational views illustrating an alternative embodiment of the present invention.

FIG. 27 illustrates another embodiment of the fluid transfer device of the present invention and a syringe.

FIG. 28 is an exploded cross-sectional view of the fluid transfer device and syringe of FIG. 27 taken along line 28—28.

DETAILED DESCRIPTION

Figure 1:
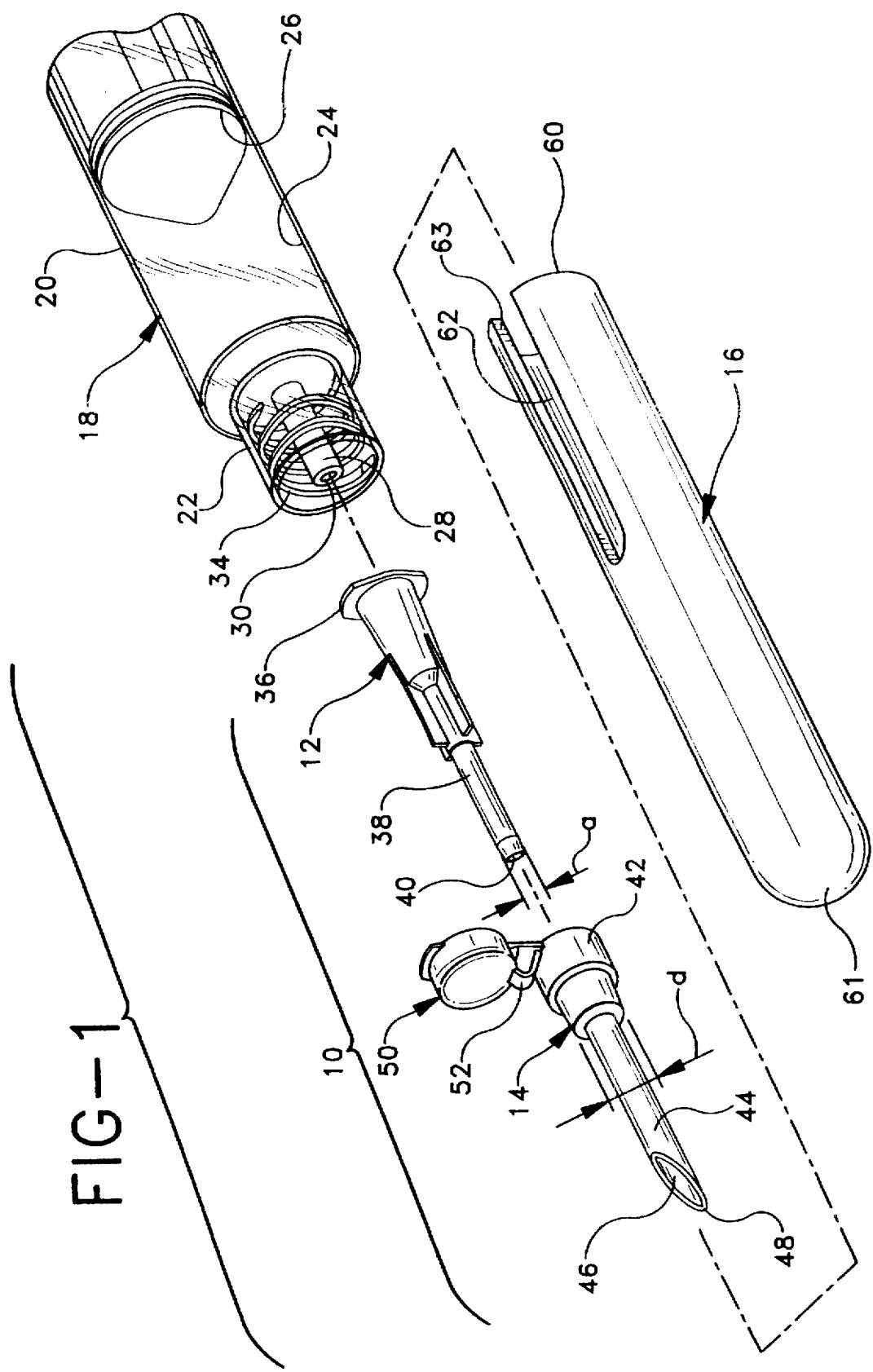
FIG. 1 is an exploded perspective view of the syringe filling device in accordance with the subject invention for accessing medication in an ampule.

While this invention is satisfied by embodiments in many different forms, there are shown in the drawings and will be herein described in detail preferred embodiments of the invention with the understanding that the present disclosure is to be considered exemplary of the principles of the invention and not intended to limit the scope of the invention to those embodiments illustrated. The scope of the invention will be measured by the appended claims and their equivalents.

Figure 2:
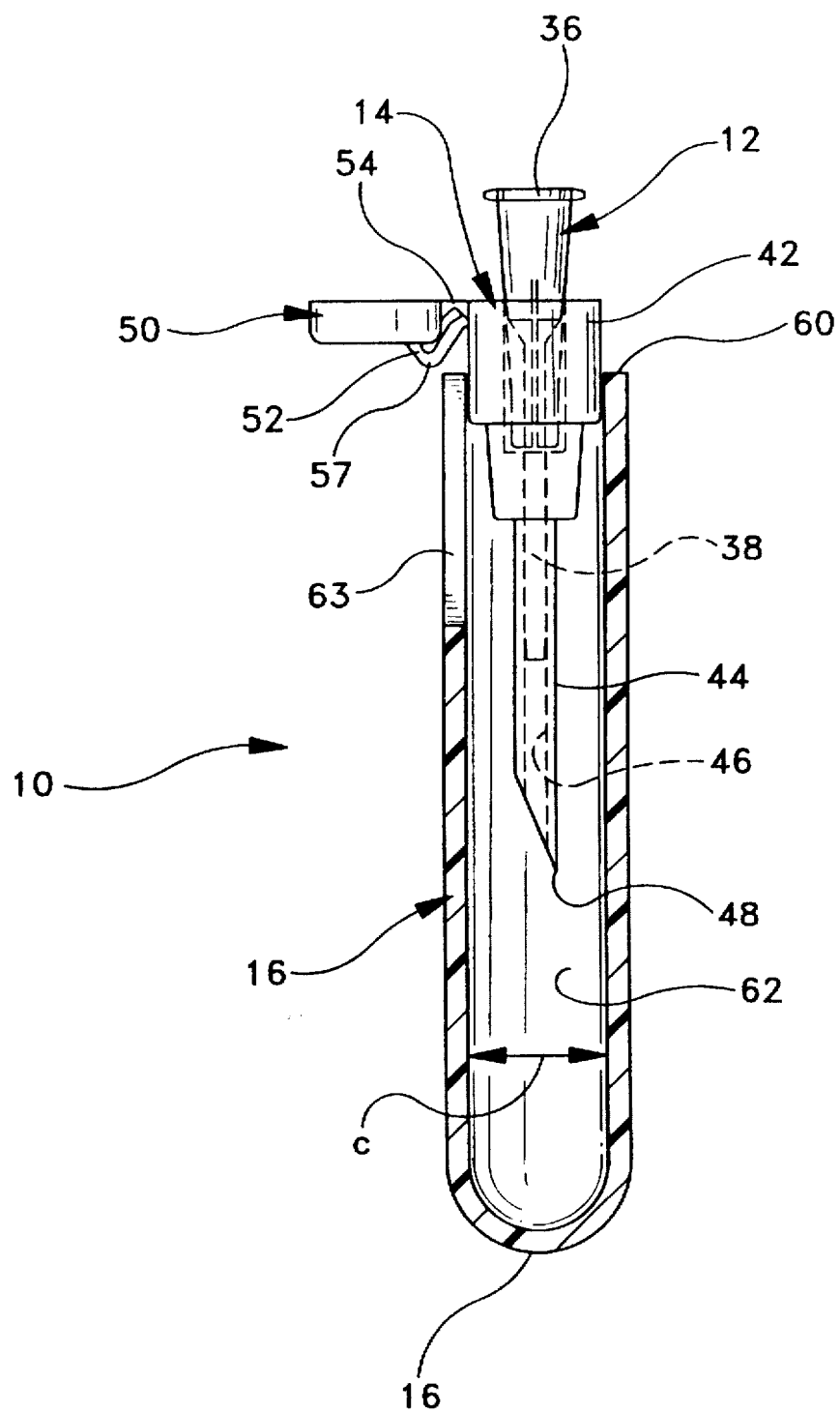
FIG. 2 is a side elevational view of the blunt cannula and vial access spike of the subject invention.

The syringe filling device in accordance with the subject invention is identified generally by the numeral 10 in FIGS. 1 and 2. Filling device 10 includes a blunt cannula 12, a vial access spike 14 and a shield 16. Filling device 10 is for use with a prior art hypodermic syringe 18. Syringe 18 includes a syringe barrel 20 having a distal end 22, a proximal end (not shown) and a fluid receiving chamber 24 therebetween. The proximal end of syringe barrel 20 is open and slidably receives a plunger 26 in fluid-tight engagement with the cylindrical wall defining chamber 24. Distal end 22 of syringe barrel 20 includes an elongate tip 28 having a passage 30 extending axially therethrough and communicating with chamber 24. The syringe preferably includes a luer collar 32 concentrically surrounding tip 28 and includes an internal thread 34.

Blunt cannula 12 of syringe filling device 10 is preferably unitarily molded from a thermoplastic material, and includes a proximal end 36, a distal end 38 and a lumen 40 extending axially therethrough. Proximal end 36 of blunt cannula 12 is configured for threaded engagement with thread 34 of luer collar 32. Distal end 38 of blunt cannula 12 is cylindrical and defines an external diameter "a". Distal end 38 also is configured for mating with an intravenous fitting having a pre-slit septum to enable delivery of fluid medication from chamber 24 of syringe barrel 20 to a patient.

Vial access spike 14 also is preferably unitarily molded from a thermoplastic material, and includes a proximal end 42, a distal end 44 and a passage 46 extending axially therethrough. Portions of passage 46 adjacent proximal end 42 are disposed in releasable fluid-tight engagement over distal end 38 of blunt cannula 12a, shown in FIG. 2. Passage 46 is cylindrical and defines an internal diameter "b" adjacent proximal end 42 of vial access spike 14 which is substantially equal to the external diameter of blunt cannula 12 adjacent distal end 38. Distal end 44 of vial access spike 14 includes a beveled tip 48 which is sufficiently sharp to be driven through the rubber stopper of a vial, as explained and illustrated further herein. However, beveled tip 48 is preferably not sufficiently sharp to penetrate skin upon incidental or accidental contact.

Figure 3:
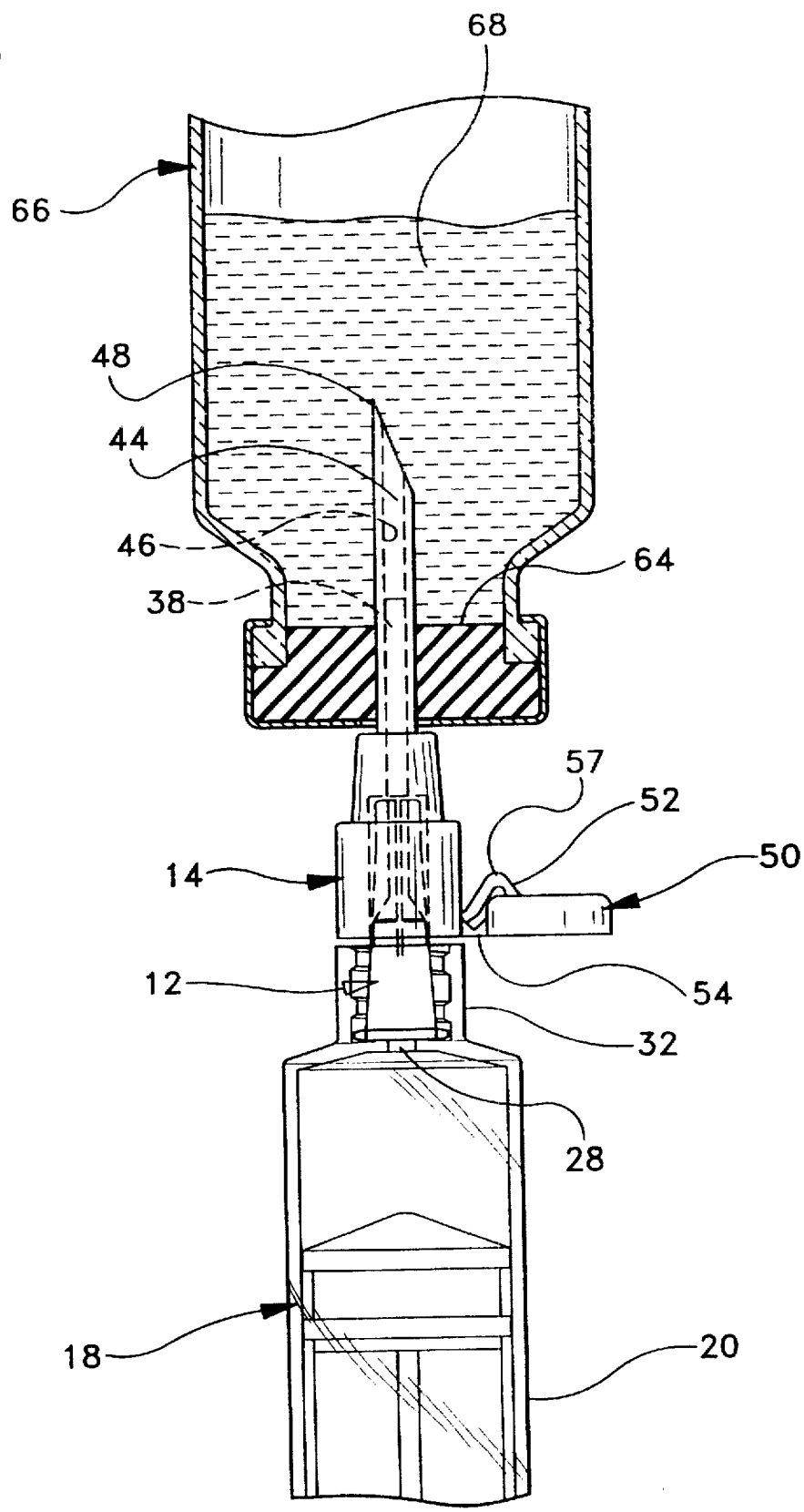
FIG. 3 shows the filling device of FIG. 2 mounted to a hypodermic syringe and accessing fluid medication in a stoppered vial.
Figure 4:
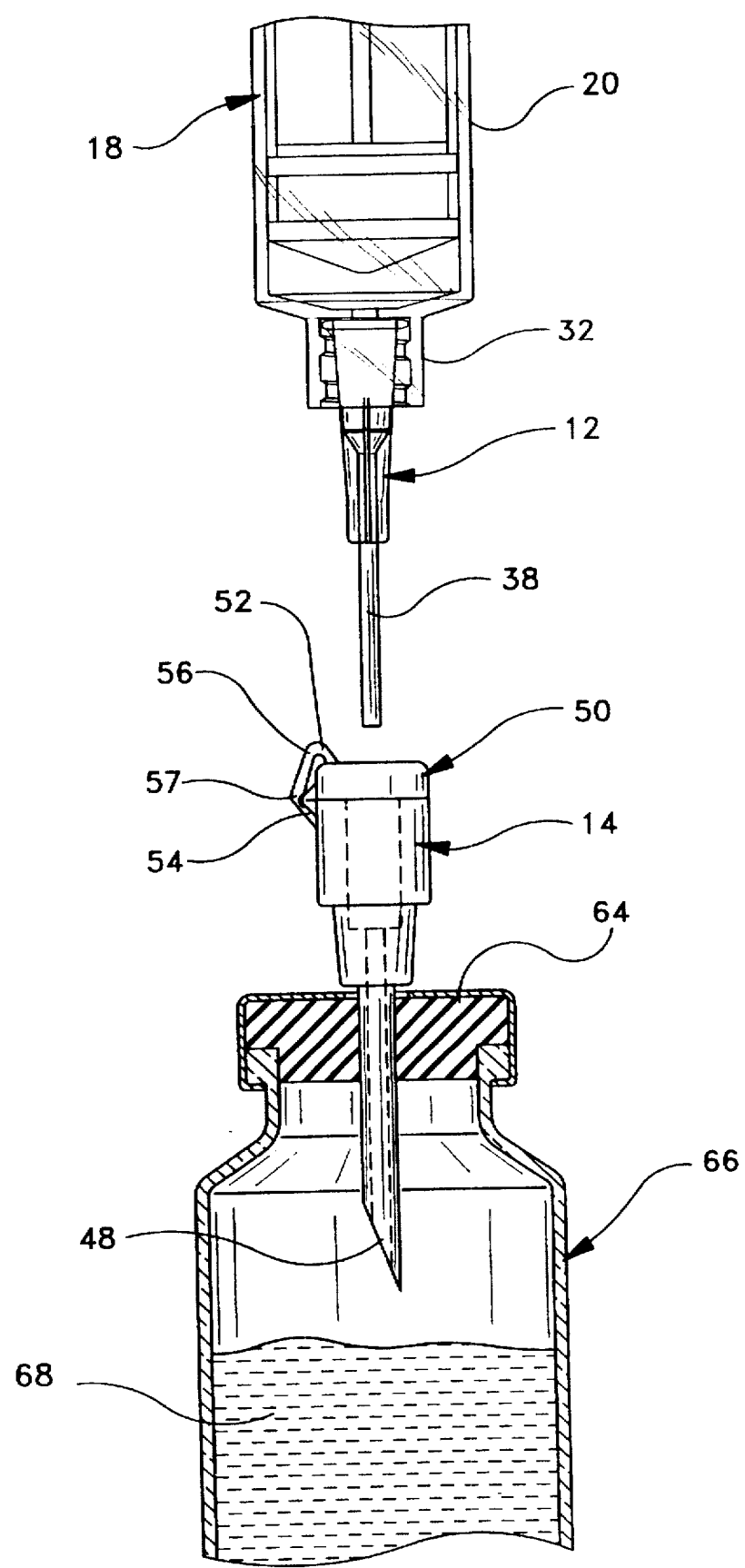
FIG. 4 is a side elevational view similar to FIG. 3, but showing the hypodermic syringe and blunt cannula separated from the vial and the vial access spike.

Vial access spike 14 further includes a cap 50 articulated to a hinge 52 which is joined to spike 14 at a location near proximal end 42. Cap 50 is dimensioned to be telescoped over proximal end 42 of vial access spike 14 for sealing substantially fluid-tight engagement. As shown in FIGS. 1–4, hinge 52 is an over center hinge with a first hinge 54 which defines an axis of rotation of cap 50. Over-center hinge 52 further includes a second hinge element 56 which defines a rotational axis parallel to, but spaced from the rotational axis of first hinge 54. Second hinge 56 is resiliently deflectable at elbow 57 and is configured to be in an unbiased condition in the fully open position of cap 50, as shown in FIGS. 1–3, or in the fully closed position as shown in FIG. 4. However, second hinge element 56 is biased at intermediate positions. The resiliency of second hinge element 56 therefore will assist any opening or closing forces exerted by a user and will urge cap 50 toward a fully opened or fully closed position.

Alternate hinge 52a, as shown in FIG. 5, defines a tether. The tether performs the function of retaining cap 50 near proximal end 42 of spike 14. However, the tether does not assist the opening or closing of cap 50.

Shield 16 is preferably formed from a thermoplastic material, and includes an open proximal end 60 and a distal end 61 which preferably is closed. A passage 62 extends into proximal end 60 and defines an inside diameter "c" which is substantially equal to outside diameter "d" of vial access spike 14 adjacent proximal end 42 thereof. Thus, proximal end 60 of shield 16 can be removably frictionally engaged over the entire vial access spike to prevent inadvertent contact with and contamination of vial access spike 14. Proximal end 60 of shield 16 is further characterized by a slot 63 which is dimensioned to surround hinge 52, and to thereby permit full seating of shield 16 over vial access spike 14.

Filling device 10 may be packaged and sold in a preassembled condition as shown in FIG. 2. More particularly, proximal end 42 of vial access spike 14 is frictionally engaged over distal end 38 of blunt cannula 12, while shield 16 may be frictionally engaged over at least portions of vial access spike 14. Alternatively filling device 10 and blunt cannula 12 may be packaged and sold in a premounted condition on hypodermic syringe 18. In this latter embodiment, shield 16 preferably is dimensioned for releasable frictional engagement over outer circumferential portions of luer collar 32. Also, vial access spike 14 and shield 16 may be sold assembled with the cap sealing the proximal end of the spike.

Filling device 10 is used with proximal end 36 of blunt cannula 12 threadedly engaged to luer collar 32 of syringe barrel 20. Shield 16 is removed shortly prior to use. Plunger 26 may then be moved proximally to draw into syringe barrel 24 a volume of air approximately equal to the desired dose of medication. Beveled tip 48 of vial access spike 14 may then be driven through rubber stopper 64 of vial assembly 66. Plunger 26 is then moved distally to urge the air from syringe chamber 24 into vial 66.

Hypodermic syringe 18 and vial 66 are inverted, as shown in FIG. 5, such that liquid medication 68 covers the portion of passage 46 of vial access spike 14 adjacent distal tip 48 thereof. Plunger 26 is then moved again in a proximal direction to draw into chamber 24 the required dose of liquid medication 68. Syringe 18 and vial assembly 66 are then inverted again such that vial assembly 66 is gravitationally below syringe 18. Syringe 18 and blunt cannula 12 then are separated from vial access spike 14 and vial 66. Syringe 18 and blunt cannula 12 may then be used in the standard manner as explained above. Vial access spike 14 can remain in rubber stopper 64 of vial 66 to enable subsequent access to medication 68. Medication 68 is sealed from the environment by rotating cap 58 about hinge 52 and into sealing engagement with proximal end 42 of vial access spike 14. Remaining medication 68 in vial 66 can be accessed subsequently by hingedly rotating cap 50 away from proximal end 42 of vial access spike 14. This subsequent access can be achieved with a conventional prior art hypodermic syringe having a blunt cannula.

As best illustrated in FIG. 6 blunt cannula 12 and vial access spike 14 are preferably connectable to each other by an interference frictional fit between the outside diameter of the blunt cannula and the inside diameter of passageway 46 of the vial access spike. The preferred blunt cannula is integrally molded of one piece of thermoplastic material. However, the blunt cannula can be made with a plastic hub and a separate blunt cannula made of a rigid material such as stainless steel joined to the hub by an adhesive or other suitable means. Lumen 40 of the blunt cannula also includes frusto-conically shaped proximal portion 41 suitable for frictionally engaging standard luer slip, as illustrated in FIG. 7, or locking luer-type syringes, as illustrated in FIG. 1.

Figure 7:
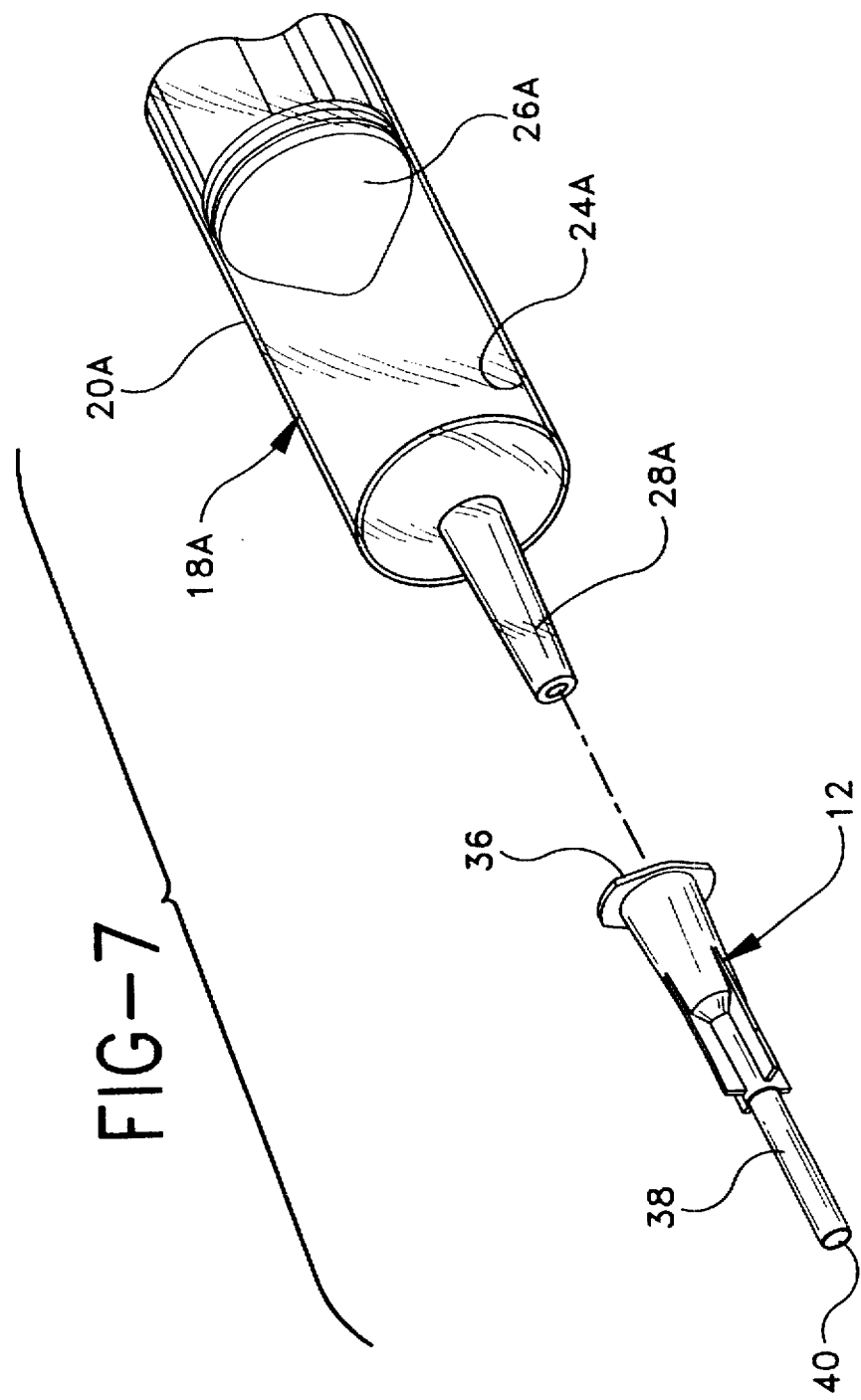
FIG. 7 is a perspective view of the blunt cannula of the present invention and a syringe aligned for assembly.

FIG. 7 illustrates a blunt cannula 12 aligned for assembly to syringe 18A having frusto-conically shaped elongate tip 28A which is adapted to frictionally and removably engage the frusto-conically shaped portion 41 of the lumen of the blunt cannula. The blunt cannula of the present invention is preferably capable of being used with locking luer type syringes, such as syringe 18, and luer slip type syringes, such as syringe 18A.

Figure 8:
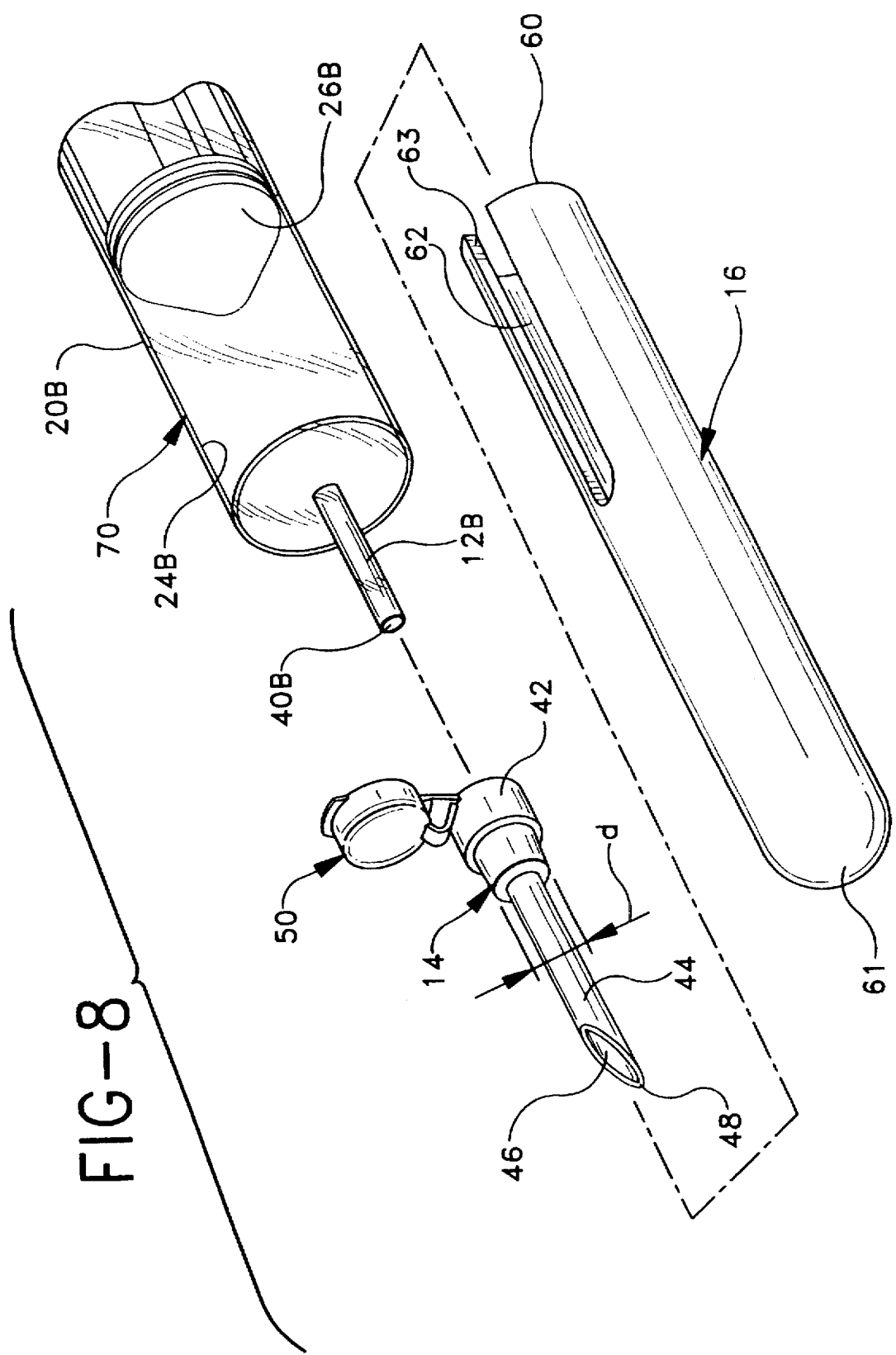
FIG. 8 is an alternative embodiment of the present invention wherein the blunt cannula and the syringe barrel are integrally molded of one piece construction.
Figure 9:
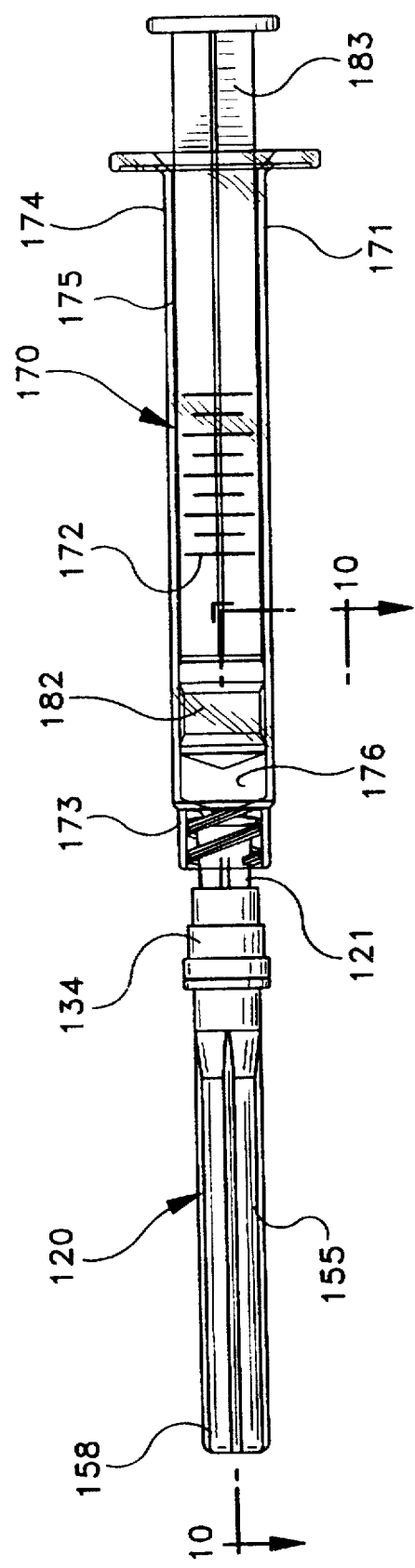
FIG. 9 is a side elevational view of the fluid transfer device of the present invention attached to a syringe.

FIG. 8 shows another embodiment of the present invention wherein syringe 70 includes integrally molded blunt cannula 12B having lumen 40B extending therethrough and in fluid communication with chamber 24B of the syringe barrel. This embodiment of the invention works substantially identically to the embodiments of FIGS. 1–7 except that the cylindrical blunt cannula cannot be separated from the syringe barrel.

While the invention has been described with respect to certain preferred embodiments, it is apparent that various changes can be made without departing from the scope of the invention as defined by the appended claims. For example, the blunt cannula of the syringe filling device may be permanently mounted to a hypodermic syringe or integrally molded as part of the syringe barrel. Additionally, the releasable engagement between the vial access spike and the blunt cannula may take forms other than the frictional engagement described and illustrated above. Still further, a metallic blunt needle cannula may be used with the vial access spike.

Adverting to FIGS. 9–21, a fluid transfer device 120 for accessing fluid from vials and ampoules comprises a cannula assembly 121 including a cannula 122 having a proximal end 123, a distal end 125 and a lumen 127 therethrough. A hub 128 having an open proximal end 129 and a distal end 131 joined to proximal end 123 of the cannula so that lumen 127 is in fluid communication with the open proximal end of the hub. Hub 128 preferably includes radial projection 132 for engaging the locking luer type collar of a syringe barrel or other fluid delivery device, as will be explained in more detail hereinafter. In this preferred embodiment, distal end 125 of the cannula includes a blunt tip 133, and the cannula and the hub are integrally formed of a thermoplastic material. However, the cannula and the hub can be separately formed and attached through various manufacturing processes with adhesives such as epoxy being preferred.

A filling straw 134 includes a proximal end 135, a distal end 137, and a passageway 138 therethrough. Filling straw 134 includes a housing 139 at proximal end 134 and a needle portion 141 at distal end 137 and a shaft portion 143 therebetween. The housing includes a cavity 144 in its proximal end in fluid communication with passageway 138. The distal end of needle portion 141 includes cutting edge 145 for piercing a vial stopper.

The cutting edge is preferably sharp enough to pierce a vial stopper but not as sharp as a needle cannula used for human injection. A point or cutting edge which is sharp enough for vial piercing and not sharp enough for human injection is evidenced in many I.V. therapy devices such as spikes or cannula for use with vials having pierceable stoppers. In this embodiment, needle portion 141 is made of metal such as stainless steel and can be held to the shaft portion using various manufacturing methods with adhesives such as epoxy being preferred. A metal needle portion offers the advantage of high strength and small diameter to reduce penetration forces as the needle portion enters the vial stopper. It is also within the purview of the instant invention to have the needle portion and the shaft portion integrally formed of a single material such as thermoplastic. In either case, it is preferred to have a shoulder 147 between the shaft portion and the needle portion to limit the depth of penetration of the needle into a vial stopper. Also, the visual appearance of the short needle portion, the pronounced shoulder and the relatively dull cutting edge communicate to the user that this straw is not intended for injection and helps assure that there will not be a mistaken attempt to use it for human injection.

Figure 10:
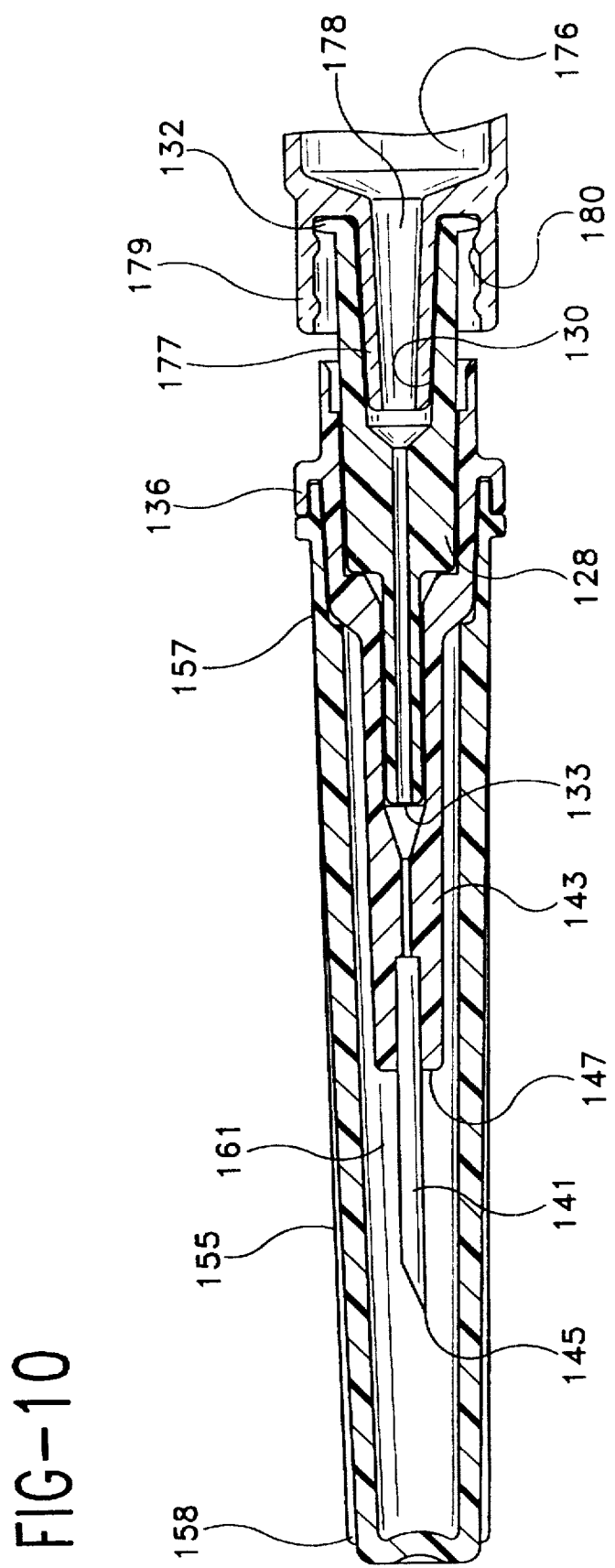
FIG. 10 is a partial cross-sectional view of a fluid transfer device and syringe of FIG. 9 taken along line 10—10.
Figure 11:
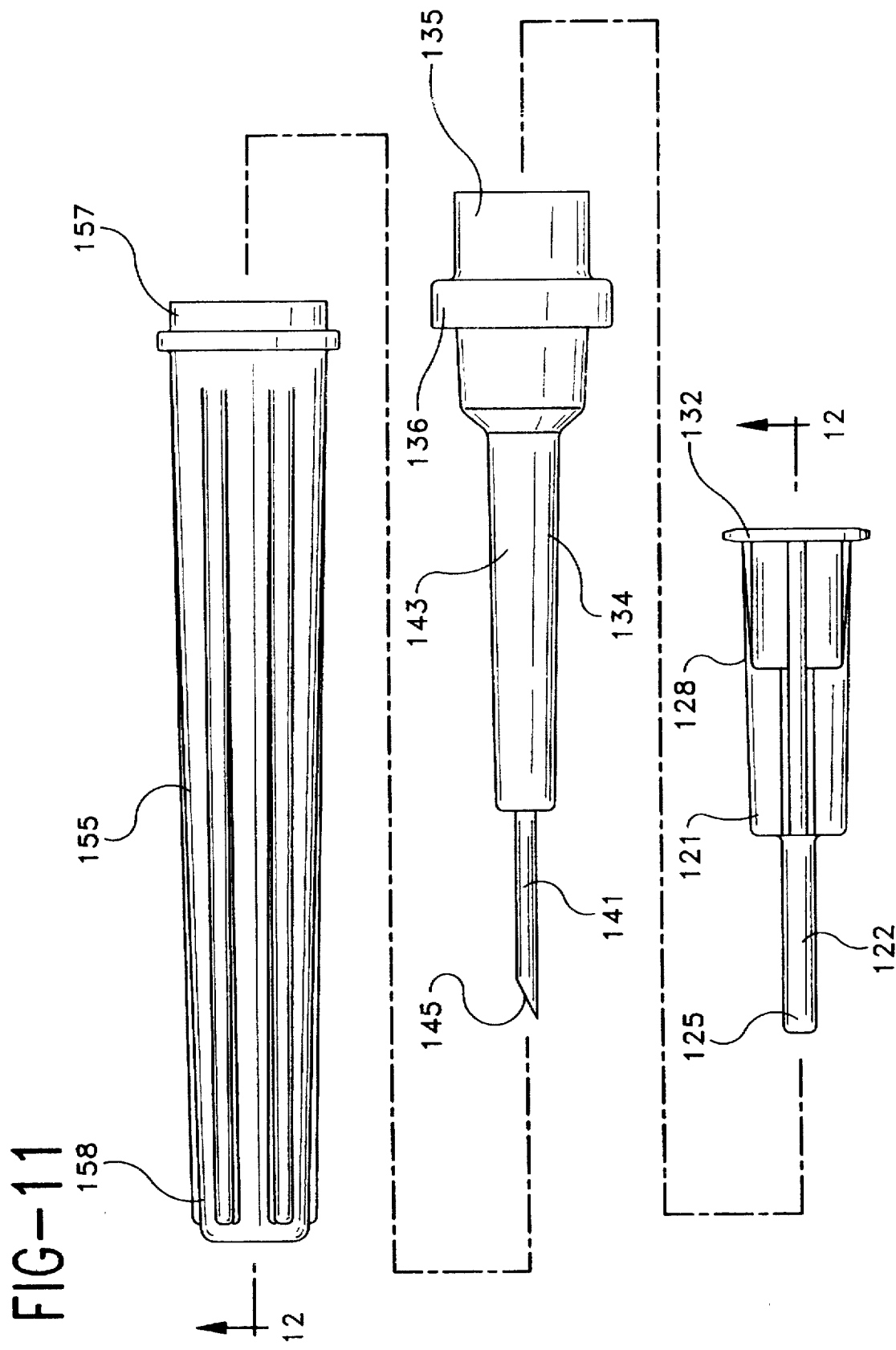
FIG. 11 is a side elevational exploded view illustrating the assembly of the fluid transfer device of the present invention.
Figure 12:
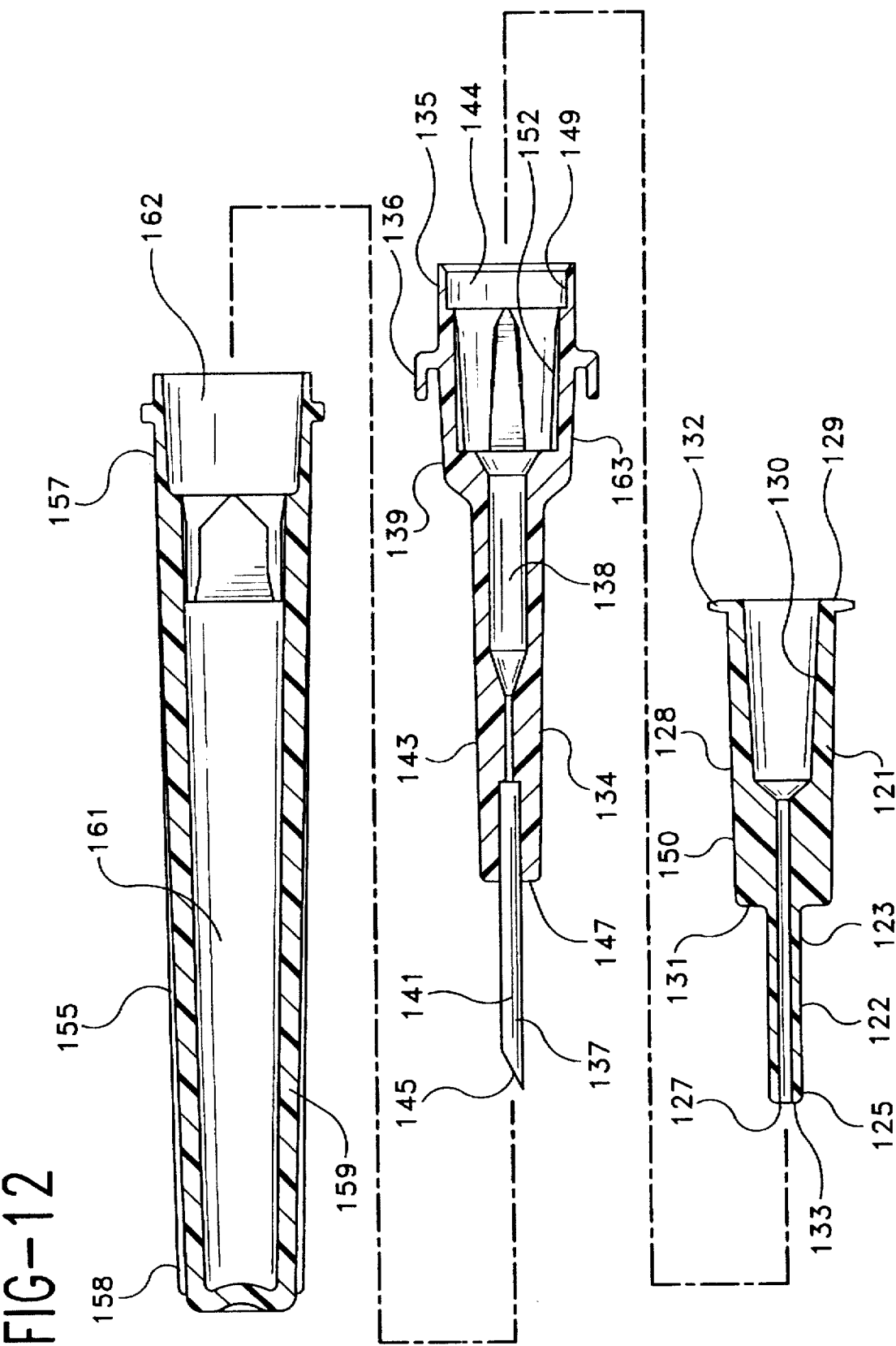
FIG. 12 is a cross-sectional view of the fluid transfer device of FIG. 11 taken along line 12—12.
Figure 13:
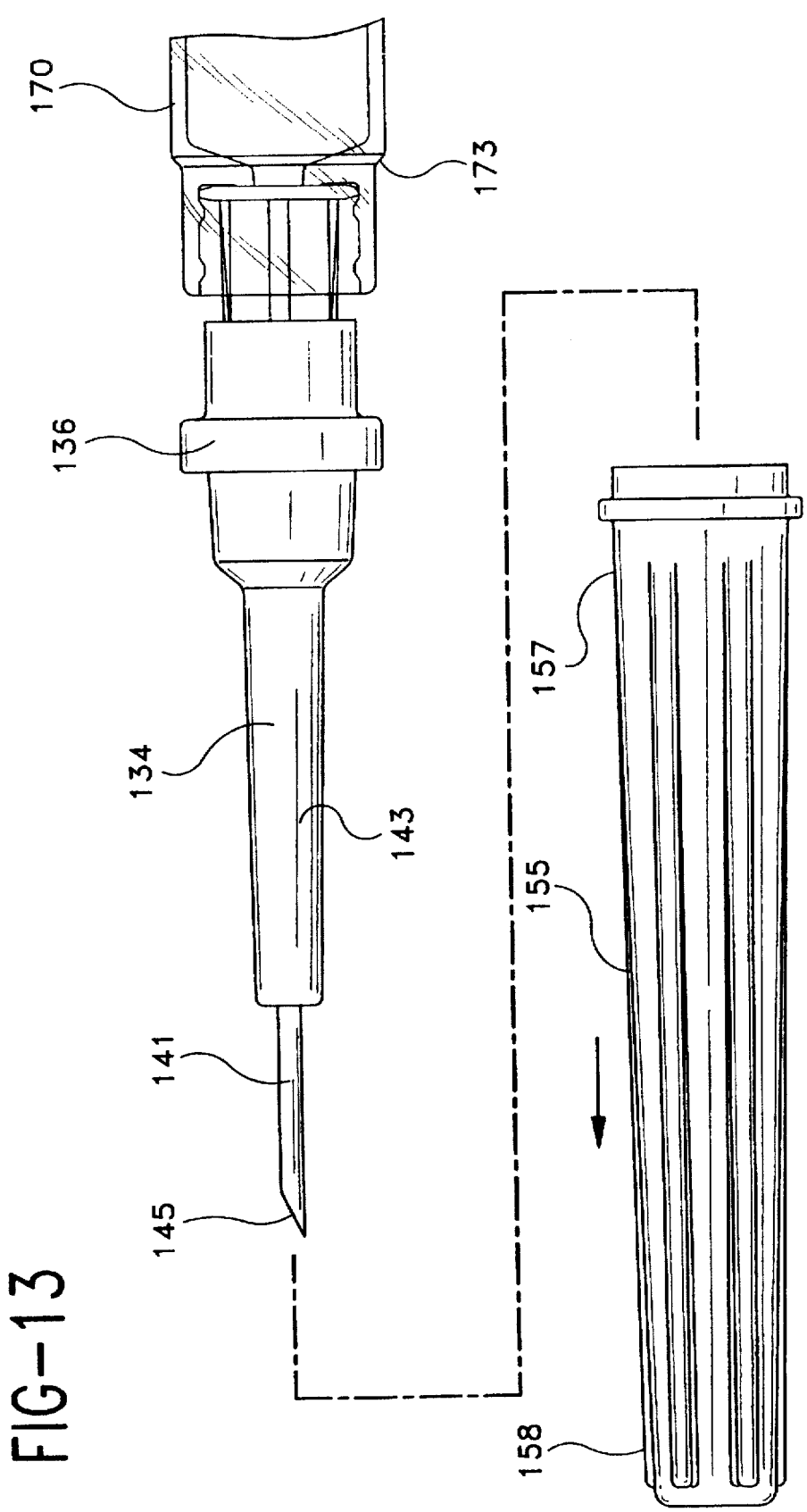
FIG. 13 is a side elevational view of the fluid transfer device attached to a syringe barrel illustrating the shield being removed.

The present invention includes means for releasably engaging the cannula assembly with the housing so that the open proximal end of the hub is in fluid communication with the passageway of the filling straw and the cannula is within the cavity or in the passageway, as best illustrated in FIG. 10. This connection should be relatively tight since fluid will be drawn through the straw and the cannula assembly into a syringe or other fluid delivery device. The means for removably engaging a cannula assembly to the housing can be accomplished by numerous structure such as threads, complementary projections and recesses and the like, with a frictional interference fit between interior surface 149 of the housing and exterior surface 150 of the needle hub being preferred. Accordingly, the housing and the hub can be releasably engaged and disengaged by moving the housing and the hub toward each other or away from each other in an axial motion. As will be explained in more detail hereinafter it is preferred that rotational force applied to the straw, through the housing, can be transmitted to the hub for engaging and disengaging the hub and a syringe barrel. This ability to transfer torque from the straw to the cannula assembly can also be accomplished by the interference fit between interior surface 149 and the housing and exterior surface 150 on the hub. However, additional structure can be provided to facilitate the transfer of torque from the straw to the cannula assembly. In this preferred embodiment, axial ribs 151 on the hub can engage axial ribs 152 in the housing to transfer torque from the straw to the cannula assembly.

A shield 155 includes an open proximal end 157, a distal end 158 and a side wall 159 therebetween defining a recess 161 and the shield. Shield 155 is removably connected to filling straw 134 so that the needle portion and preferably the shaft portion of the straw are within the recess.

Numerous structures can be used to achieve the removable connection between the shield and the straw such as threads, projections and recesses to accomplish a snap-fit arrangement, and interference fits. In this preferred embodiment, interior proximal surface 162 in the shield frictionally engaged exterior surface 163 on the housing. Accordingly, axial force may be used to remove and re-install the shield on the straw. Interior surface 162 and exterior surface 163 are preferably frusto-conically shaped to provide smooth frictional engagement. It is an important feature of this preferred embodiment that interior proximal surface 162 of the shield also releasably engages exterior surface 150 on the hub so that the shield can be used to shield the straw or, when the straw is removed, to shield the cannula assembly. This is an important feature because it allows different methods for using the fluid transfer device of the instant invention, depending on the preference of the user.

The fluid transfer device of the present invention is suitable for use with fluid delivery devices such as syringes. For the purpose of illustration, fluid transfer device 120 is connected to a hypodermic syringe 170 comprising a syringe barrel 171 having a distal end 173, a proximal end 174 and a circular side wall 175 defining a chamber 176 for retaining fluid. Volume measuring indicia 172 are on the barrel for measuring the dose of liquid to be delivered. The distal end of the syringe barrel is connected to hub 128 so that the lumen of cannula 122 is in fluid communication with chamber 176 of the syringe barrel. In this embodiment, distal end 173 of the syringe barrel includes a frusto-conically shaped tip 177 having a conduit therethrough which provides a fluid path between the cannula and the chamber. The frusto-conically shaped tip of the syringe barrel frictionally engages a preferably frusto-conically-shaped surface 130 in open proximal end 129 of the hub. The distal end of the syringe barrel also preferably, but not necessarily, includes a locking luer-type collar 179 concentrically surrounding tip 177. The luer collar has an internal thread 180 which engages the radial projection 132 on hub 128 to hold it securely to the barrel. It is within the scope of the present invention to include various hub configurations to attach to a variety of other medical fluid handling devices. The hub configuration described hereinabove, having a frusto-conically shaped interior cavity, reflects one of these many possibilities. Many syringes and fluid handling devices, such as stopcocks and adapters, and other fluid handling devices contain luer slip and locking luer type fittings to which a hub having a frusto-conically shaped interior cavity will properly engage. It is within the purview of the present invention to provide a fluid transfer device wherein the cannula assembly is integrally molded with the syringe barrel.

A stopper 182 is positioned in chamber 176 in sliding fluid-tight engagement with circular side wall 175. A rigid elongate plunger rod 183 is connected to the stopper and extends proximally through the open proximal end of barrel 171. The stopper and the plunger rod can be made of one-piece unitary construction. Force applied to the plunger rod causing sliding movement of the stopper in a proximal direction draws fluid through conduit 178 into chamber 176. Conversely, sliding movement of stopper 182 in a distal direction urges fluid from chamber 176 through conduit 178.

Figure 14:
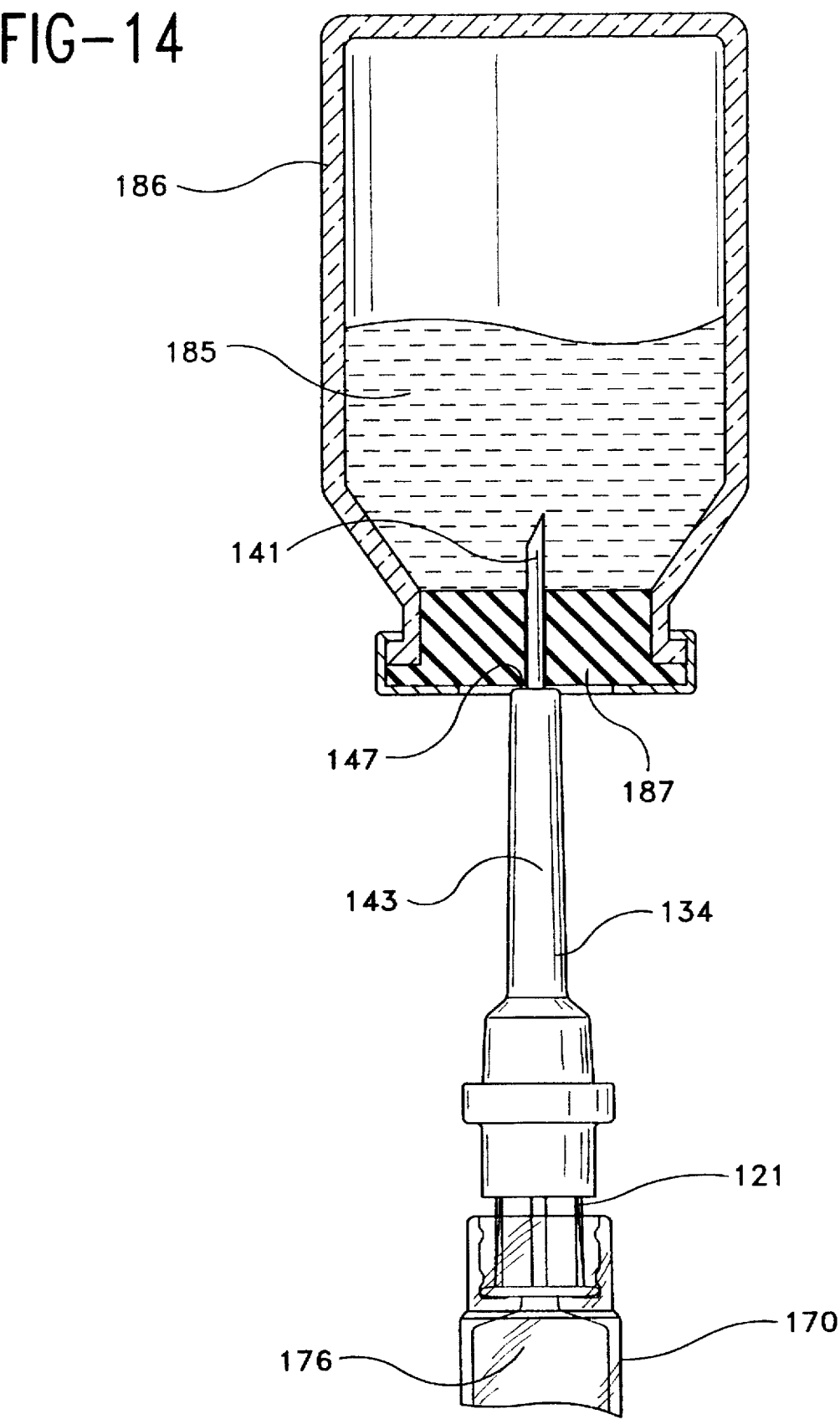
FIG. 14 is a side-elevational view illustrating the fluid transfer device and syringe being used to withdraw injectable liquid from a vial having a pierceable stopper.

The fluid transfer device 120 of the present invention, coupled with a fluid delivery device, such as a hypodermic syringe 170, can be used to access fluid in a vial or an ampoule and deliver said fluid to the injection site of an I.V. set or catheter. As illustrated in FIG. 14, the fluid transfer device 120 can be used with syringe 170 to access injectable liquid or medication, such as fluid 185, contained within a vial 186 having a pierceable stopper 187. The fluid is accessed by piercing stopper 187 with needle portion 141 of filling straw 134. Shoulder 147 between needle portion 141 and shaft portion 143 on the filling straw will limit the penetration of the needle portion into the vial. In the preferred embodiment the needle portion is approximately 10 mm long and has a diameter of about 1.3 mm. Initially, an volume of air approximately equal to the desired dosage is injected into the vial. The vial is then inverted, as illustrated in FIG. 14, and the fluid is withdrawn into the syringe by action of the plunger in a proximal direction to urge fluid 185 from the vial 186 through passageway 138 of the filling straw, the lumen of the cannula and into the chamber 176 of the syringe barrel. The user will compare the axial position of the plunger with volume measuring indicia 172 on the cylindrical side wall to insure that the desired dose is obtained. It can be seen that the level of fluid 185 in the vial will gradually decrease as fluid is drawn into the chamber of the syringe barrel. Shoulder 147 keeps the distal end of the needle portion close to the stopper to make it easy to withdraw almost all of the liquid from the vial. Also, the short length of the needle portion coupled with the shoulder and the larger shaft portion sends a clear message to the medical practitioner that this device is not intended for injection into humans.

Figure 15:
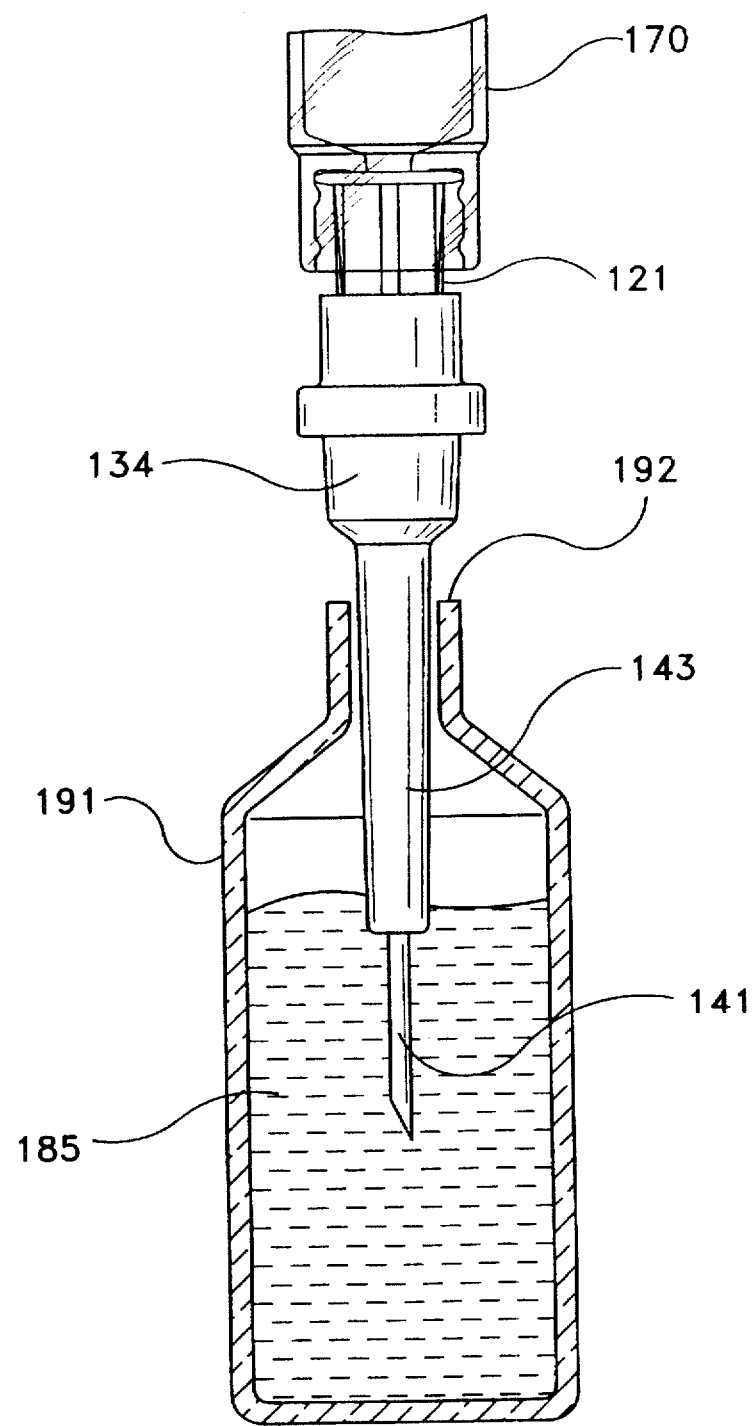
FIG. 15 is a side elevational view of the fluid transfer device and syringe being used to withdraw injectable liquid from an ampoule.

As best illustrated in FIG. 15 the fluid transfer device of the present invention can also be used to withdraw fluid 185 from ampoule 191. As noted above, at the time of use the neck portion of the ampoule is snapped or severed leaving an open neck 192. Because the ampoule does not have an elastomeric seal it is not inverted during the transfer of fluid from the ampoule to a hypodermic syringe. Accordingly, a long filling straw, capable of reaching toward the bottom or the sides of the ampoule is required. For this purpose, shaft portion 143 of the filling straw is provided. The long shaft portion in conjunction with the needle portion enables the fluid transfer device of the present invention to effectively remove liquid from an ampoule. In the preferred embodiment the shaft portion is approximately 15 mm long and has an outside diameter of about 3 mm. As with the vial, fluid is withdrawn from the ampoule into the chamber of the syringe through action of the plunger so that fluid is drawn through the passageway in the straw, the lumen of the cannula assembly and into the chamber.

Figure 21:
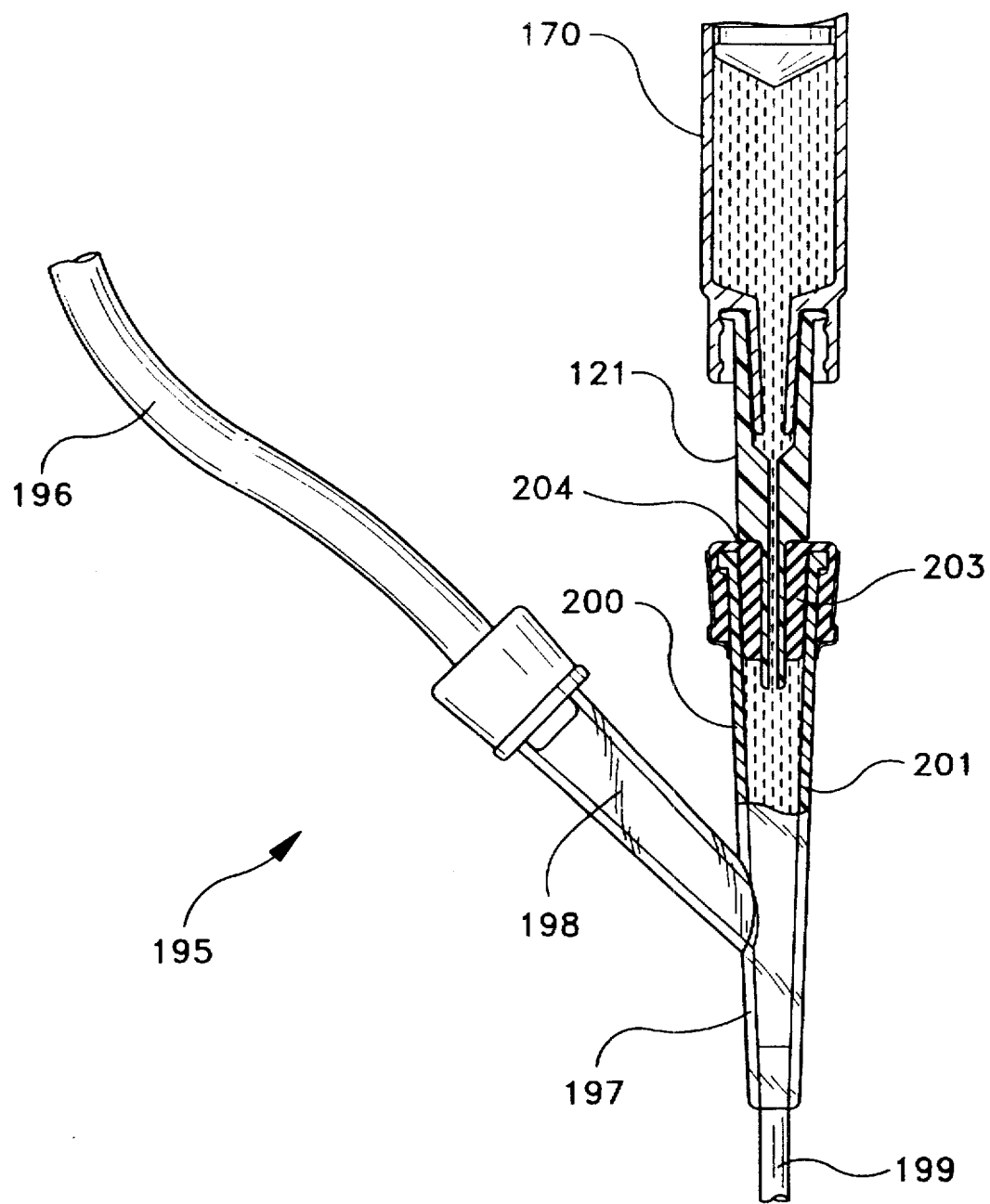
FIG. 21 is a side elevational view of injectable liquid being delivered to an injection site in an I.V. set using the cannula assembly of the present invention and a syringe.

Referring to FIGS. 9–21, with particular emphasis on FIGS. 16–21, it can be seen that there are two separate methods which can be used to deliver medication from the syringe to the injection site through an I.V. set or other catheter device having an injection site. The first method, as illustrated in FIGS. 16, 17 and 21. In this first method, after the syringe is filled with fluid from a vial or ampoule or other source, shield 155 is placed over filling straw 134 so that the shield is removably connected to the straw and needle portion 141 and shaft portion 143 are contained within recess 161 of the shield. This is the same assembly as existed at the beginning of the filling process. In this preferred embodiment, engagement between the shield and the straw is accomplished by axial motion which causes structure on the open proximal end of the shield to engage the housing on the filling straw. The filled syringe is then delivered to the point of use. At the point of use, the user will remove the assembly of the shield and straw from the cannula assembly by grasping the straw, preferably at raised portion 136 on the straw, and applying an axial force to remove the straw from the cannula assembly, as illustrated in FIG. 17. Since the cannula assembly is attached to the syringe through the locking luer collar, the connection between the cannula assembly and the syringe barrel is stronger than the frictional engagement between the filling straw and the cannula assembly, so that the actual force applied will not remove the cannula assembly from the syringe. Depending on the structures of the various parts, the forces can be balanced so that the desired result is obtained with respect to removing components. The syringe is now ready for delivering medication, as will be described hereinafter in more detail.

The second method for using the fluid transfer device of the present invention, as best illustrated in FIGS. 18–21, requires the user to remove filling straw 134 immediately after the syringe is filled with fluid from a vial or ampoule by grasping the filling straw, preferably by enlarged portion 136, and applying an axial distal force to the straw to remove it from the cannula assembly. Shield 155 is then placed over the cannula assembly, as illustrated in FIG. 19 to protect the cannula until the time of use. The second method is possible because hub 128 of the cannula assembly and housing 139 of the filing straw have similar exterior shapes so that shield 155 can engage either the hub or the housing. In this preferred embodiment the engagement is frictional and engagement and disengagement can be accomplished by applying axial forces. At the time of use, as illustrated in FIG. 20 shield 155 is removed from the cannula assembly by applying a distal axial force.

The preferred embodiment of the fluid transfer device of the present invention includes a cannula having a blunt distal end for use with I.V. sets or other catheter devices having injection sites with pre-slit septums. Specifically, as illustrated in FIG. 21, an I.V. set 195 can include a housing 197 having a hollow interior conduit 198 and a flexible tube 199 connected to the vascular system of the patient, usually through a catheter. Housing 197 also contains flexible tube 196 which is connected to a source of I.V. fluid. Housing 197 also includes port 200 having a conduit 201 therethrough in communication with the hollow interior. A septum 203 covers the end of the conduit or as positioned within the conduit. The most common ports are covered by pierceable septums or pre-slit septums and are known in the art and sometimes referred to as "PRN" from the Latin pro re nata meaning "as the need arises." The septum is preferably made of rubber or another elastomeric material which permits insertion of a sharp needle cannula in order to infuse fluids into or to withdraw fluids from the catheter. Upon withdrawal of the needle cannula, the septum seals itself As illustrated in FIG. 21, septum 203 is a pre-slit septum having a slit 204 therein. Septum 203 effectively seals conduit 201 from the exterior of the housing. However, access to the conduit can be achieved by pressing blunt tip 133 of cannula 122 against the area of the septum containing slit 204. Gentle force applied to the syringe assembly in an axial direction will cause the blunt distal end of the cannula to enter the conduit through the slit which is forced open by the blunt cannula. Upon removal of the blunt cannula from the conduit, the slit portion of the septum automatically seals itself. Since housing 197 is connected to the patient's vascular system medication can be given to the patient through the PRN port without additionally piercing the patient's vein or, in this case, without the use of a sharp needle.

It is an important feature of the present invention that the entire process of filling the syringe from a vial or ampoule with a fluid, such as an injectable liquid or medication, and the delivery of this fluid to the patient can be accomplished by using the cannula assembly of the present invention alone and without the use of any injection needles. The most common prior art way to withdraw medication from a vial with a pierceable septum is to attach a standard hypodermic needle assembly, illustrated in FIG. 23, to a hypodermic syringe. The fluid is drawn into the syringe barrel and then the needle is discarded and a blunt cannula is attached to the syringe. This additional step creates an opportunity to an accidental needle stick and requires the presence of some form of disposal system. Wherein the present invention, in its preferred embodiment, does not use a standard needle and does not require a disposal step since all of the components of the fluid transfer device can stay with the syringe until the time of use, at which time, all components are suitably disposed of. Also, the present invention provides a fluid transfer device which allows for filling a syringe and delivering the medication to the patient without the use of a sharp injection cannula.

Figure 22:
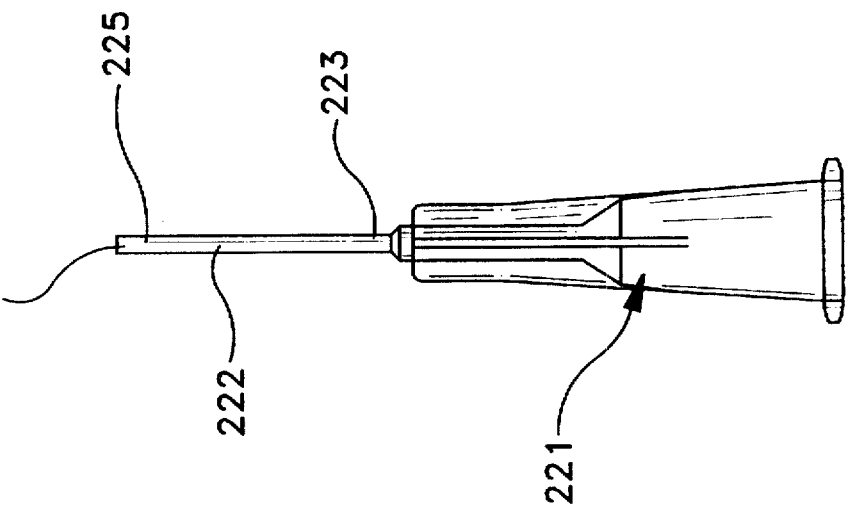
FIG. 22 illustrates an alternative cannula assembly.

FIG. 22 illustrates an alternative cannula assembly 221 including a metal cannula 222, preferably made of stainless steel. Cannula 222 includes a proximal end 223 and, distal end 225, having a lumen therethrough. Distal end 225 also includes blunt tip 233. Cannula assembly 221 functions substantially as cannula assembly 121 except that the cannula is made of metal. Stainless steel cannula are desirable because of their great strength advantage over thermoplastic cannula which allows such cannula to be made in smaller outside diameters and a large lumen diameter while still having substantial strength.

Figure 23:
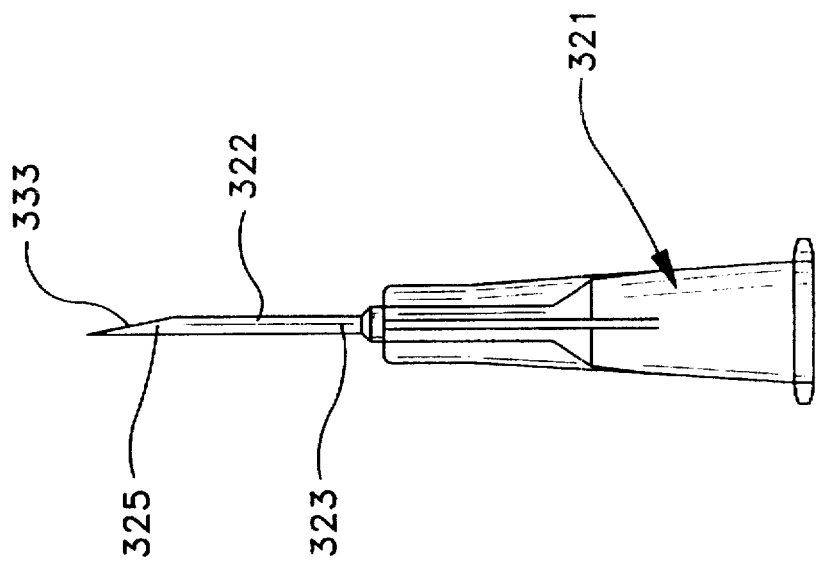
FIG. 23 illustrates a standard hypodermic needle.

FIG. 23 illustrates a prior art needle assembly 321 which is commonly used to inject medication into a patient and for transferring fluid through pierceable septums such as septums found in a medication vials and I.V. sets. Needle assembly 321 includes needle cannula 322 having a proximal end 323, a distal end 325 and a lumen therethrough. Distal end 325 further includes a sharp point 333 capable of piercing skin, flexible stoppers and septums.

The preferred embodiment of the fluid transfer device of the present invention includes a cannula assembly having a blunt cannula for use which allows the use of one device for filling a syringe through a vial or ampoule and delivering the fluid from the vial or ampoule through a pre-slit septum of an I.V. set or other catheter device. Accordingly, the preferred embodiment is a needleless system for filling and delivering injectable fluid which does not require a sharpened needle cannula or an additional step of disposing of such cannula after the syringe is filled. However, it is within the purview of the present invention to include a fluid transfer device which contains a needle assembly having a needle cannula with a sharpened distal tip such as needle assembly 321. In usages where a pre-slit septum is not available in the catheter or I.V. set, a sharpened steel needle cannula must be used. However, even with a needle assembly having a sharpened needle cannula, the fluid transfer device of the present invention offers a clear advantage over the prior art in that the needle assembly stays with the syringe from the time of filling through the time of injection and there is no additional step of removing a sharpened needle cannula from the syringe after filling the syringe and no additional complications regarding the disposal of the sharpened needle cannula in this intermediate step. Also the needle cannula is protected from damage during the filling procedure.

FIGS. 24 and 25 illustrate an alternative fluid transfer device of the present invention. The fluid transfer device of FIGS. 24 and 25 functions substantially the same way as the fluid transfer device of FIGS. 9–20 except that structure is provided so that the removal of the filling straw from the cannula assembly requires a rotational motion. Specifically, alternative fluid transfer device 420 includes a cannula assembly 421 having a cannula 422 and a hub 428. Hub 428 further includes a locking luer collar 424 having an internal thread 426. Filling straw 434 includes a housing 439 having a radial projection 440 configured to engage internal thread 426 of luer collar 424. Accordingly, attachment of the filling straw to the cannula assembly is accomplished by a rotational motion. A shield 455 is removably connected to the straw. The straw and the shield are configured so that the shield can be removed and reconnected to the straw through axial motion of the shield with respect to the straw. This alternative embodiment of the present invention offers a distinct advantage to the user since the shield is removable from the straw through axial motion and the straw is removable from the cannula assembly through rotational motion further assuring that the user will not accidentally remove one component when he or she intends to remove another.

Figure 26:
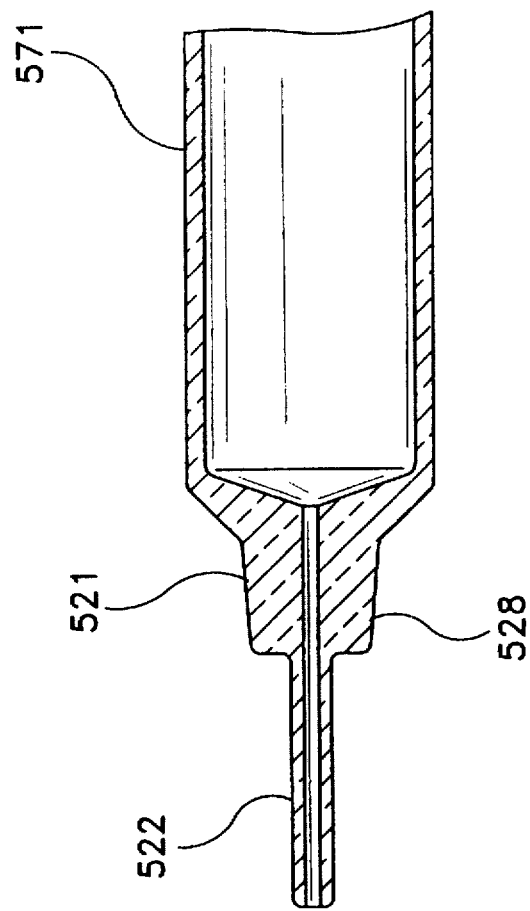
FIG. 26 illustrates another embodiment of the present invention wherein the cannula and the syringe barrel are integrally formed in one piece.

FIG. 26 illustrates an alternative structure of the fluid transfer device of the present invention wherein the cannula or the cannula assembly is integrally formed with a syringe barrel. Specifically, cannula assembly 521 which includes cannula 522 and hub 528 is integrally molded with syringe barrel 571 so that the cannula is not removable from the syringe barrel. Other than this feature the syringe and blunt cannula function substantially the same way as the embodiment illustrated in FIGS. 9–21.

FIGS. 27–28 illustrate an alternative fluid transfer device 600. This fluid transfer device 600 is intended for use in applications where a separate cannula assembly is not required. Fluid transfer device 600 includes a filling straw 634 having a proximal end 635, a distal end 637 and a passageway 638 therethrough. The straw includes a housing 639 at said proximal end, a needle portion 641 at said distal end, and a shaft portion 643 therebetween. The needle portion and the shaft portion are preferably integrally molded of thermoplastic material. The housing includes a preferably frusto-conically shaped cavity 644 in its proximal end in fluid communication with passageway 638. A cutting edge 645 at the distal end of the needle portion is provided for piercing a vial stopper. A shield 655 having an open proximal end 657, a distal end 658 and a side wall 659 therebetween defining a recess 661 in the shield. The shield is removably connected to the straw so that the shaft portion and the needle portion of the straw are preferably contained within the recess. A syringe 670 having an elongate cylindrical body 671 defining a chamber 676 for retaining fluid, an open proximal end, a distal end 673 and a frusto-conically shaped tip 677, extending from the distal end and having a tip passageway 678 therethrough in fluid communication with the chamber. The tip is positioned within cavity 644 of housing 639 so that chamber 676 is in fluid communication with passageway 638 of the filling straw. Cavity 644 in the housing includes a frusto-conically shaped wall 646 configured to frictionally engage the frusto-conically shaped tip on the syringe barrel. There are needleless systems comprising valves and special fittings which are designed to accept the standard frusto-conically shaped tip of a hypodermic syringe barrel. With these systems a separate cannula assembly is not necessary since the tip portion of the syringe barrel acts as the cannula in the system. In all other respects the embodiment of FIGS. 27 and 28 function substantially the same as the embodiment of FIGS. 9–20 with the exception that the fluid is delivered through the tip of the syringe into the fluid receiving device which could even be a pre-slit septum designed to accept a standard syringe tip.

In this embodiment, it is preferred but not necessary that the syringe include a locking luer-type collar 679 having an internal thread 680. The proximal end of housing 639 includes radial projection 632 which is adapted to engage thread 680 to further enhance the connection between the housing and the syringe barrel. In this embodiment, it is preferable that shield 655 includes a radial projection 640 so that the shield can engage the luer collar when the filling straw is removed, so that after filling the syringe the straw may be discarded and the syringe tip reshielded with shield 655 for delivery to the point of use. In the alternative, the filled syringe with shielded straw attached may be taken to the point of use wherein the shield and the straw are removed together and discarded as described hereinabove in using the embodiments of FIGS. 9–20.

Figure 29:
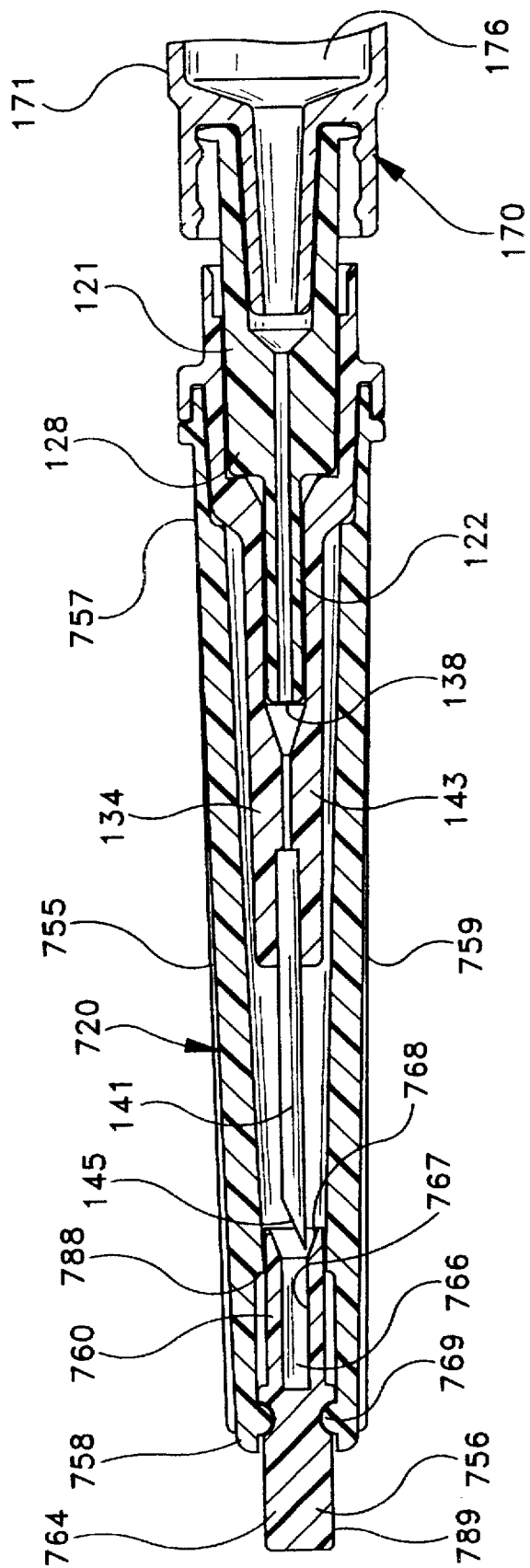
FIGS. 29 and 30 are cross-sectional side elevation views having an alternative embodiment of the present invention including a shield having a movable seal plug.
Figure 30:
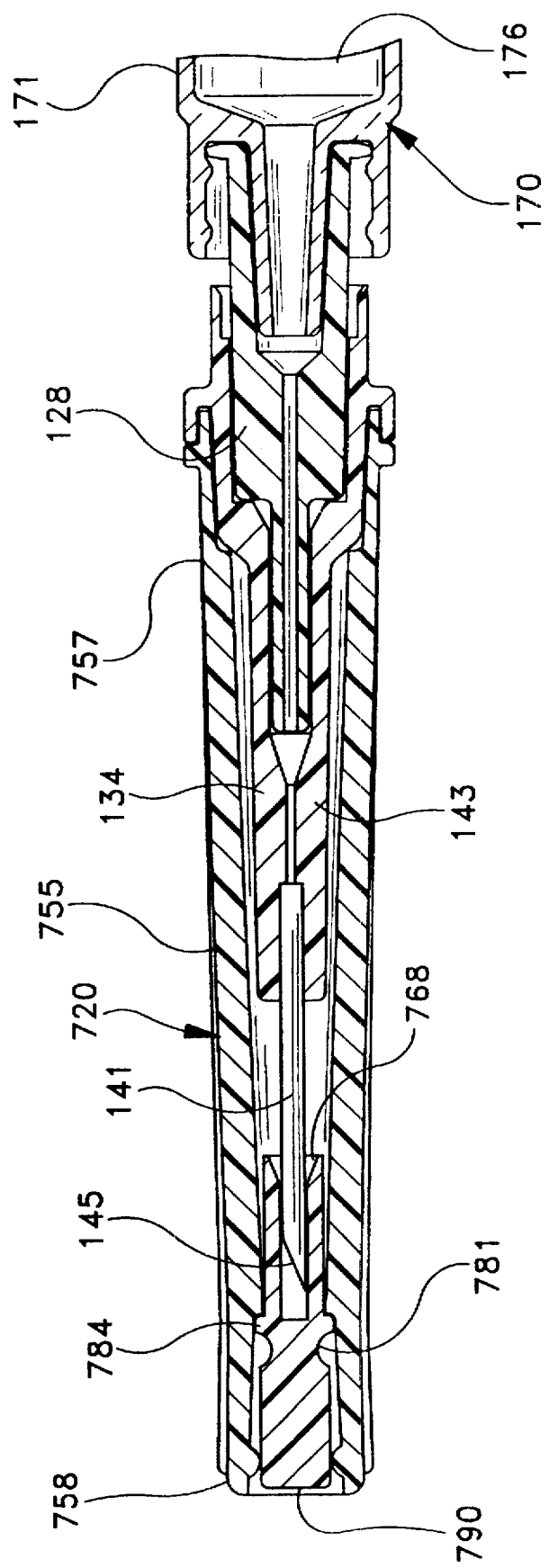

FIGS. 29 and 30 illustrate an alternative fluid transfer device 720. In some respects fluid transfer device 720 functions similarly to the fluid transfer device of FIGS. 9–21. For the purposes of description, elements in fluid transfer device 720 which are the same as elements in the embodiment of FIGS. 9–21 are given the same reference numerals. Fluid transfer device 720 includes cannula assembly 121 having cannula 122 and hub 128. The filling straw 134 includes needle portion 141 having cutting edge 145 at its distal end. The cannula assembly and the straw are removably engaged. Fluid transfer device 720 is connected to syringe 170 having an elongate cylindrical body 171 defining a chamber 176 for retaining fluid.

A shield 755 includes an open proximal end 757, an open distal end 758 and a side wall 759 therebetween defining a recess 761 in the shield. The shield is removably connected to the filling straw so that shaft portion 143 and needle portion 141 are substantially contained within recess 761. A seal plug 756 includes a proximal end 760 and a distal end 764. The seal plug has a distal position, as illustrated in FIG. 29, wherein the seal plug projects distally outwardly from distal end 758 of shield 755 for telescoping movement from the distal position to a proximal position, illustrated in FIG. 30. The seal plug includes means for sealing the needle portion to prevent unpressurized fluid from communicating between passageway 138 of the filling straw and the exterior of the shield, when the seal plug is in the proximal position. In this embodiment, means for sealing includes retention conduit 766 extending distally from the proximal end of the seal plug. The retention conduit includes an inside surface 767 for sealing engagement with the needle portion of the filling straw when the sealing plug is in the proximal position as illustrated in FIG. 30. It is preferable to include a tapered portion 768 at the proximal end of the seal plug for guiding the needle portion into the retention conduit when the seal plug is being moved from the distal position to the proximal sealing position.

In some applications it is preferred to provide structure, or to configure the components, so that in the normal use of the fluid transfer device 720, seal plug 756 cannot be moved from its proximal sealing position to its distal position. In this embodiment means for preventing the seal plug from moving from the proximal sealing position to the distal position is provided by configuring the plug so that in the proximal sealing position the plug is substantially within open distal end 758 of shield 755. By being substantially within or completely within the open distal end of the shield, digital access to the plug for the purposes of moving in a proximal direction is severely limited or completely limited. Means for preventing movement of the seal plug from its proximal sealing position can also be provided by interacting structure between the shield and the plug. Such structure may have components on the inside or the outside of the shield depending on the structure of the plug. Such structure can include projections and/or recesses on the shield to engage projections and/or recesses on the seal plug when the seal plug is in said proximal position.

The seal plug may be held in its distal position through mechanical interaction between the shield and the seal plug such as interfering structures, friction, threads or the like. In this embodiment, the shield includes inwardly directed projection 769 and the seal plug includes recess 781. When the seal plug is in its distal position projection 769 is positioned in recess 781 holding the seal plug in its desired axial position with respect to the shield. The projection may be of any size from a discrete bump to a full annular ring, or a segmented ring depending on the structural shapes and the choice of materials for the plug and the shield. Likewise, the recess in the seal plug can take a variety of configurations to appropriately mate with the projection in the shield. Also, the structure can be reversed so that the projection is on the seal plug and the recess is in the shield.

To move the seal plug to its proximal sealing position, the user can apply digital pressure to finger contact surface 790 at distal end 764 of the seal plug. In this embodiment, as the seal plug moves proximally, tapered portion 768 guides, where necessary, the distal end of needle portion 141 into the retention conduit 766 of the seal plug. In this embodiment, inside surface 767 of the retention conduit is configured to contact the exterior surface of needle cannula 141 for a sealing engagement. The inside surface can be continuous as illustrated or some other sealing structure such as one or more inwardly projecting rings which provide a seal. Proximal motion of the seal plug with respect to the shield may be limited by additional structure or by configuring the components. For example, if the seal plug is completely within the shield, proximal motion of the seal plug, through digital application will cease when the finger contact surface of the plug is aligned with the distal end of the shield. In this embodiment further structure is provided to limit the proximal motion of the seal plug with respect to the shield. This structure includes protuberance 784 on the seal plug and ledge 788 in the shield. In its proximal sealing position protuberance 784 will contact ledge 788 to provide resistance to further proximal motion and feedback to the user that the seal plug is in the proximal sealing position. The physical engagement of the seal plug with respect to the needle portion may be all that is needed to hold the seal plug in its proximal sealing position. Although not necessary, this embodiment preferably includes additional structure for holding the seal plug in its proximal sealing position. This structure includes exterior surface 789 of the seal plug being larger than the space provided in the open end of the shield at projection 769 so that there is a frictional engagement between the seal plug and the shield as illustrated in FIG. 30. All of the structures recited hereinabove for holding said seal plug in its distal position are within the purview of the present invention for holding the seal plug in its proximal sealing position.

In use, the fluid transfer device 720 is filled in the same manner described for the embodiment of FIGS. 9–21. After filling, the shield is re-installed over the straw. The user then applies digital pressure to finger contact surface 790 of the seal plug to move the seal plug from the distal position, as illustrated in FIG. 29, to the proximal sealing position, as illustrated in FIG. 30. At this point the entire fluid path from chamber 176 in syringe barrel 171 through the passageway in the needle portion of the straw is sealed to protect the contents from the environment and to help prevent unpressurized loss of the contents to the environment. This feature allows the medication containing fluid transfer device and syringe to be stored for a longer period of time than an unsealed system such as the embodiment of FIGS. 9–21. This is an important feature of this embodiment of the present invention.

Figure 31:
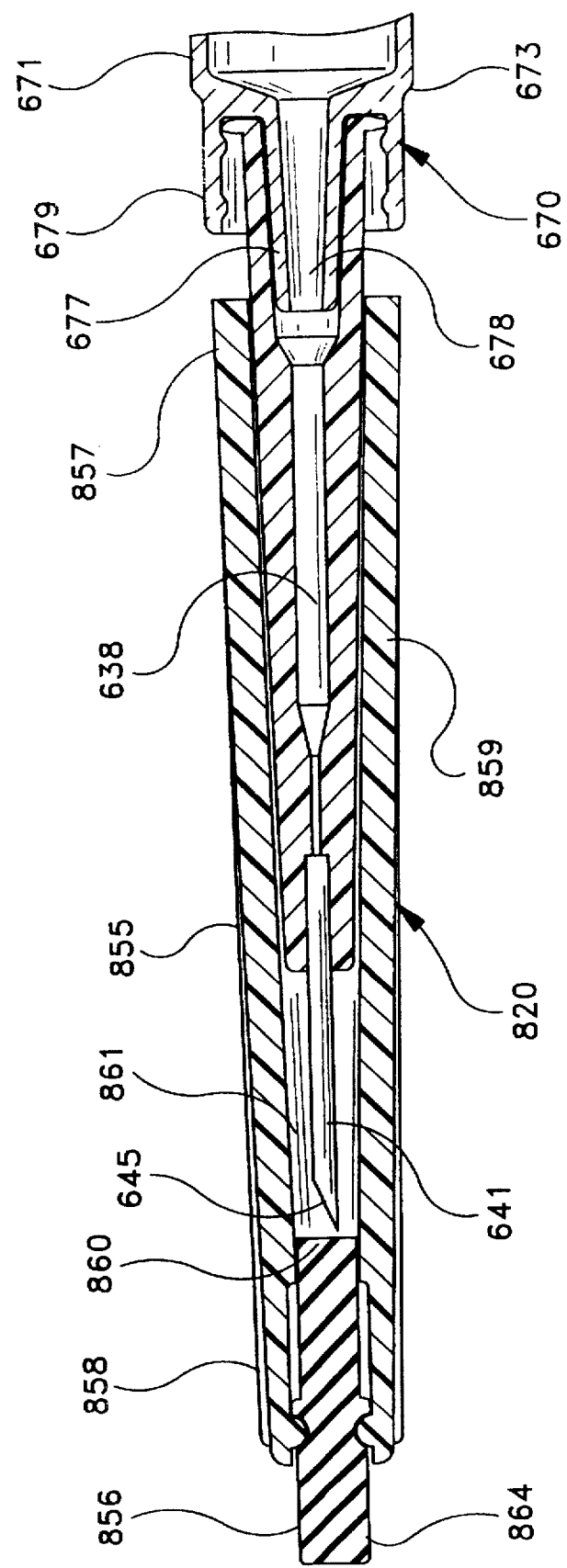
FIGS. 31 and 32 are cross-sectional side elevation views having another alternative embodiment of the present invention including a shield having a movable seal plug.
Figure 32:
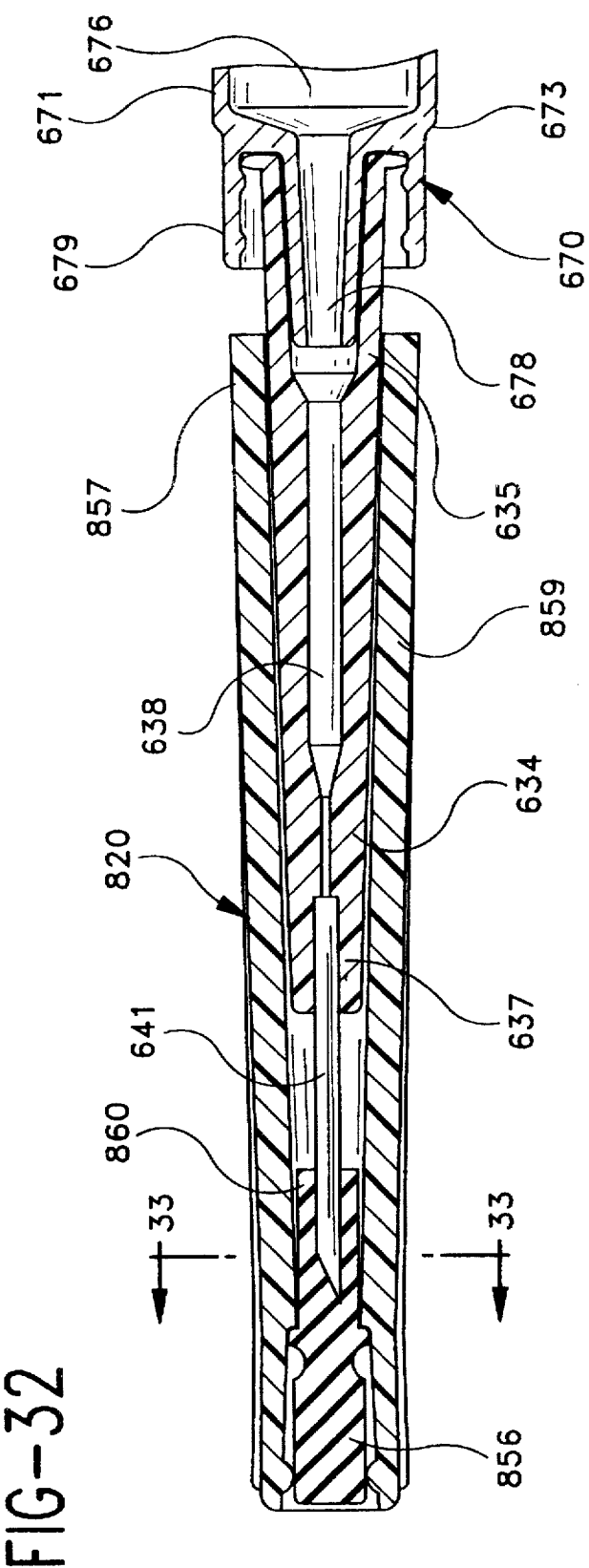
Figure 33:
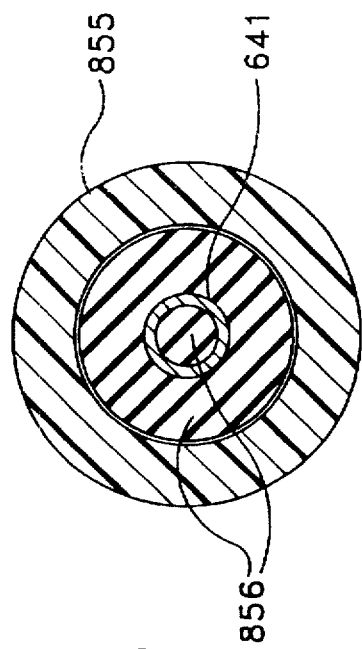
FIG. 33 is a cross-sectional view of the fluid transfer device of FIG. 32 taken along line 30—30.

FIGS. 31–33 illustrate an alternative fluid transfer device 820 which is similar to the embodiment of FIGS. 27 and 28 with a shield and seal plug assembly which is similar, but not identical, to the embodiment of FIGS. 29 and 30. For the purposes of illustration, fluid transfer device 820 is connected to syringe 670 having an elongate cylindrical body 671 defining a chamber 676 for retaining fluid, an open proximal end, a distal end 673 and a frusto-conically shaped tip 677, extending from the distal end and having a tip passageway 678 therethrough in fluid communication with chamber 676. Filling straw 634 includes a proximal end 635, a distal end 637 and a passageway 638 therethrough. The straw is connected to tip 677 of the syringe so that passageway 638 is in fluid communication with chamber 676.

A shield 855 having an open proximal end 857, an open distal end 858 and a side wall 859 therebetween defining a recess 861 in the shield. The shield is removably connected to the filling straw so that the shaft portion and the needle portion are contained substantially within the recess.

A seal plug 856 includes a proximal end 860 and a distal end 864. The seal plug has a distal position wherein the seal plug projects distally outwardly from the distal end of the shield for telescoping movement from the distal position, as illustrated in FIG. 31, to a proximal position, as illustrated in FIG. 32, wherein the seal plug seals the needle portion to prevent unpressurized fluid communication between the passageway and the exterior of the shield.

Although a wide variety of materials such as, natural rubber, synthetic rubber, thermoplastic elastomer and thermoplastic can be used to fabricate the seal plug of the present invention, softer materials such as natural rubber, synthetic rubber and thermoplastic elastomers are preferred for seal plug 856 of the present embodiment. In this embodiment, the components are configured such that needle portion 641 is long enough so that when seal plug 856 is in the proximal position, as illustrated in FIG. 32, the distal end of needle portion 641 is embedded in proximal end 860 of the seal plug. Depending on the shape of the cutting edge 645 of the needle portion and the configuration and material of the seal plug, embedding the needle portion into the seal plug will cause the seal plug to sealingly engage the outside surface of the needle portion, occlude the passageway therethrough, as illustrated in FIG. 33, or both, to prevent unpressurized fluid communication between the passageway and the exterior of the shield. Fluid transfer device 820 is used in a similar manner to the embodiment of FIGS. 29 and 30.

Figure 34:
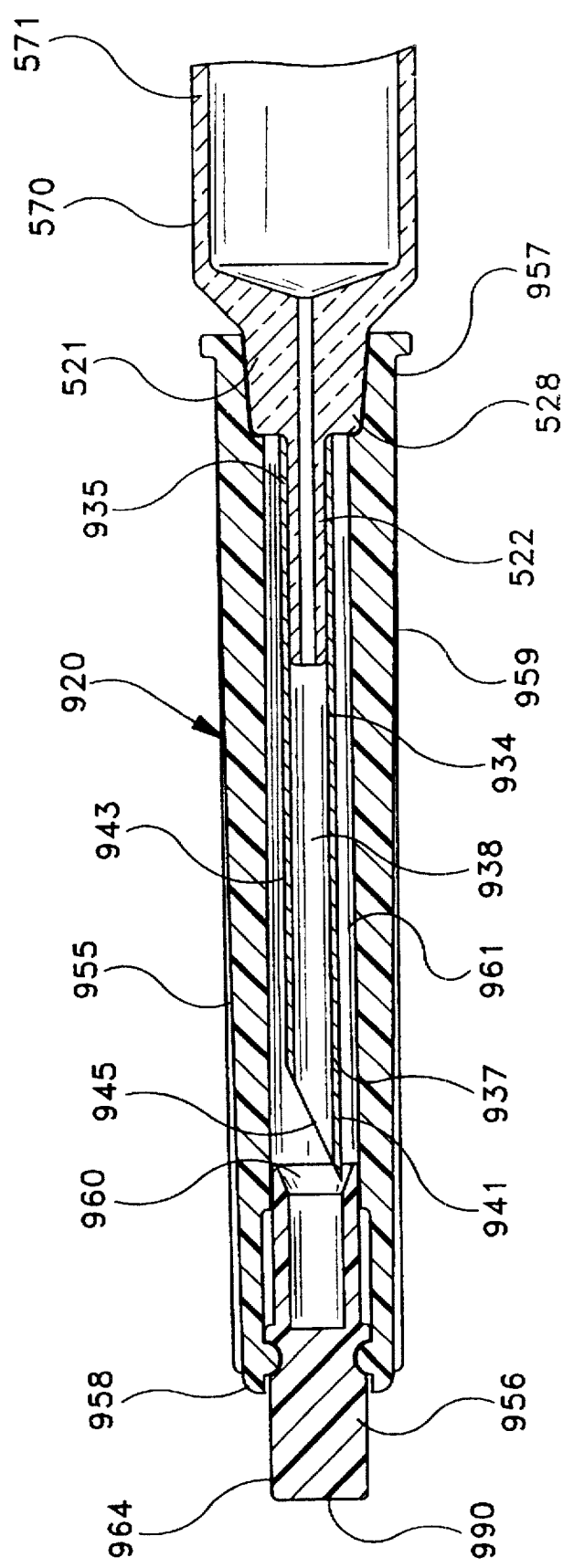
FIG. 34 is a cross-sectional side elevation view having still another alternative embodiment of the present invention including a shield having a movable seal plug.

FIG. 34 illustrates an alternative fluid transfer device 920 which is attached to cannula assembly 521 which includes cannula 522 and hub 528 which are integrally formed with syringe barrel 571. A filling straw 934 includes a proximal end 935, a distal end 937 and a passageway 938 therethrough. Filling straw 934 includes a needle portion 941 at its distal end and a shaft portion 943 between the needle portion 941 and proximal end 935. A cutting edge 945 at the distal end of the needle portion is provided for piercing a vial stopper. The cannula assembly and the filling straw are removably engaged. A shield 955 has an open proximal end 957, an open distal end 958 a side wall 959 therebetween defining a recess 961 in the shield. The shield is removably connected to the filling straw so that the needle portion and substantially all of the shaft portion are contained within the recess.

A seal plug 956 includes a proximal end 960 and a distal end 964. The seal plug has a distal position, as illustrated in FIG. 34, wherein the seal plug projects distally outwardly from distal end 958 of shield 955 for telescoping movement from the distal position to a proximal position wherein the seal plug seals the needle portion to prevent unpressurized fluid communication between the passageway and the exterior of the shield.

In use, the syringe is filled using the filling straw, as generally described hereinabove, and the shield is replaced as illustrated in FIG. 34. The user can then apply a proximally directed force to finger contact surface 990 on the seal plug to move the seal plug into the proximal sealing position.

What is claimed is:

1. A fluid transfer device for accessing fluid from vials and ampoules comprising:

a cannula assembly including a cannula having a proximal end, a distal end and a lumen therethrough, and a hub having an open proximal end and a distal end joined to said proximal end of said cannula so that said lumen is in fluid communication with said open proximal end of said hub;

a filling straw having a proximal end, a distal end and a passageway therethrough, said straw including a housing at said proximal end, a needle portion at said distal end and a shaft portion therebetween, said housing having a cavity in its proximal end in fluid communication with said passageway, a cutting edge at the distal end of said needle portion for piercing a vial stopper, and said cannula assembly and said filling straw being removably engaged so that said open proximal end of said hub is in fluid communication with said passageway of said filling straw;

a shield having an open proximal end, an open distal end and a side wall therebetween defining a recess in said shield, said shield being removably connected to said filling straw so that said shaft portion and said needle portion are contained substantially within said recess; and a seal plug having a proximal end and a distal end, said seal plug having a distal position wherein said seal plug projects distally outwardly from said distal end of said shield for telescoping movement from said distal position to a proximal position, said seal plug including means for sealing said needle portion to prevent unpressurized fluid communication between said passageway and the exterior of said shield when said seal plug is in said proximal position.

2. The fluid transfer device of claim 1 wherein said means for sealing includes a retention conduit extending distally from said proximal end of said seal plug, said conduit having an inside surface for sealing engagement with said needle portion when said sealing plug is in said proximal position.

3. The fluid transfer device of claim 2 wherein said seal plug includes a tapered portion at said proximal end for guiding said needle portion into said retention conduit when said seal plug is being moved from said distal position to said proximal position.

4. The fluid transfer device of claim 1 wherein said sealing means includes said needle portion being long enough so that when said seal plug is in said proximal position said distal end of said needle portion is embedded in said proximal end of said seal plug.

5. The fluid transfer device of claim 1 wherein said seal plug is made of material selected from the group consisting of natural rubber, synthetic rubber, thermoplastic elastomer and thermoplastic.

6. The fluid transfer device of claim 1 further including means for preventing said seal plug from moving from said proximal sealing position to said distal position.

7. The fluid transfer device of claim 1 wherein said open proximal end of said shield is configured to releasably engage said hub when said filling straw is removed from said hub.

8. The fluid transfer device of claim 1 wherein said distal end of said cannula includes a blunt distal tip.

9. The fluid transfer device of claim 1 wherein said cannula and said hub are integrally formed of thermoplastic material.

10. The fluid transfer device of claim 1 wherein said cannula is formed of metal.

11. The fluid transfer device of claim 1 further including a syringe barrel having an elongate cylindrical body defining a chamber for retaining fluid, an open proximal end, a distal end and a tip extending from said distal end having a tip passageway therethrough in fluid communication with said chamber, said tip being positioned within said open proximal end of said hub so that said chamber is in fluid communication with said lumen of said cannula.

12. The fluid transfer device of claim 1 wherein said cannula assembly is integrally formed with a syringe barrel having an elongate cylindrical body defining a chamber for retaining fluid, an open proximal end and a distal end, said cannula extending from said distal end of said barrel and positioned so that said lumen of said cannula is in fluid communication with said chamber.

13. A fluid transfer device for accessing fluid from vials and ampoules comprising:

a cannula assembly including a cannula having a proximal end, a distal end and a lumen therethrough, and a hub having an open proximal end and a distal end joined to said proximal end of said cannula so that said lumen is in fluid communication with said open proximal end of said hub;

a filling straw having a proximal end, a distal end, and a passageway therethrough, said straw including a needle portion at said distal end and a shaft portion between said needle portion and said proximal end, a cutting edge at the distal end of said needle portion for piercing a vial stopper, and said cannula assembly and said filling straw being removably engaged so that said open proximal end of said hub is in fluid communication with said passageway of said filling straw;

a shield having an open proximal end, an open distal end and a side wall therebetween defining a recess in said shield, said shield being removably connected to said filling straw so that said needle portion and substantially all of said shaft portion are contained within said recess; and a seal plug having a proximal end and a distal end, said seal plug having a distal position wherein said seal plug projects distally outwardly from said distal end of said shield for telescoping movement from said distal position to a proximal position wherein said seal plug seals said needle portion to prevent unpressurized fluid communication between said passageway and the exterior of said shield.

14. The fluid transfer device of claim 13 further including a syringe barrel having an elongate cylindrical body defining a chamber for retaining fluid, an open proximal end, a distal end and a tip extending from said distal end having a tip passageway therethrough in fluid communication with said chamber, said tip being positioned within said open proximal end of said hub so that said chamber is in fluid communication with said lumen of said cannula.

15. The fluid transfer device of claim 14 wherein said open proximal end of said shield is configured to releasably engage said distal end of said syringe barrel when said filling straw is removed from said syringe barrel.

16. A method for transferring injectable liquid including comprising the steps of:

(a) providing a syringe including a syringe barrel having an elongate cylindrical body defining a chamber for retaining fluid, an open proximal end, a distal end and a tip extending from the said distal end having a tip passageway therethrough in fluid communication with said chamber, a stopper in fluid-tight slidable engagement inside said barrel and an elongate plunger rod connected to said stopper and extending proximally through said open proximal end of said barrel;

(b) providing a syringe filling device comprising a cannula assembly including a cannula having a proximal end, a blunt distal end and a lumen therethrough, and a hub having an open proximal end and a distal end joined to said proximal end of said cannula so that said lumen is in fluid communication with said open proximal end of said hub; a filling straw having a proximal end, a distal end and a passageway therethrough, said straw including a, a needle portion at said distal end and a shaft portion between said needle portion and said proximal end, a cutting edge on the distal end of said needle portion for piercing a vial stopper, said cannula assembly being removably engaged with said filling straw so that said open proximal end of said hub is in fluid communication with said passageway of said filling straw; a shield having an open proximal end, an open distal end, and a side wall therebetween defining a recess in said shield, said shield being removably connected to said straw so that said shaft portion and said needle portion are contained within said recess; and a seal plug having a proximal end and a distal end, said seal plug having a distal position wherein said seal plug projects distally outwardly from said distal end of said shield for telescoping movement from said distal position to a proximal position wherein said seal plug seals said needle portion to prevent unpressurized fluid communication between said passageway and the exterior of said shield;

(c) connecting said syringe filling device to said syringe so that said tip is positioned within said open proximal end of said hub and said chamber is in fluid communication with said cannula;

(d) providing a vial having a pierceable septum and containing an injectable liquid;

(e) removing said shield from said straw;

(f) piercing said pierceable septum of said vial with said needle portion of said filling straw to establish fluid communication between the interior of the vial and the chamber of the syringe;

(g) withdraw the desired amount of injectable liquid from said vial into said chamber by moving said plunger rod in a proximal direction with respect to said barrel;

(h) withdrawing said needle portion from said septum of said vial;

(i) reconnecting said shield to said straw so that said shaft portion and said needle portion of said straw are contained within said recess of said shield; and (j) moving said seal plug from said distal position to said proximal position to seal said needle portion.

17. The method of claim 16 further comprising the steps of:

(k) moving said syringe to an I.V. set having an injection site with a pre-slit septum;

(l) removing said shield and said straw from said cannula assembly; and (m) advancing said syringe into said pre-slit septum so that said blunt tip of said cannula pierces said septum and establishes fluid communication with said I.V. set; and (n) advancing said plunger so that said piston moves said fluid from said chamber through said lumen into said I.V. set.

\* \* \* \* \*